US007430598B2

(12) United States Patent
Raden et al.

(10) Patent No.: US 7,430,598 B2
(45) Date of Patent: Sep. 30, 2008

(54) SYSTEMS AND METHODS FOR HEALTH MONITOR ALERT MANAGEMENT FOR NETWORKED SYSTEMS

(75) Inventors: Gary P. Raden, Seattle, WA (US); Eduardo da Fonseca Melo, Bellevue, WA (US); Tolga Bayram Ekmekci, Bellevue, WA (US); Thomas M. Soemo, Bothell, WA (US); Lisa M. Butler, Seattle, WA (US); Richard J. Moerloos, Jr., Seattle, WA (US)

(73) Assignee: Microsoft Corporation, Redmond, WA (US)

( * ) Notice: Subject to any disclaimer, the term of this patent is extended or adjusted under 35 U.S.C. 154(b) by 1151 days.

(21) Appl. No.: 10/722,009

(22) Filed: Nov. 25, 2003

(65) Prior Publication Data
US 2005/0114174 A1 May 26, 2005

(51) Int. Cl.
G06F 15/16 (2006.01)
G06F 15/173 (2006.01)
G06F 15/177 (2006.01)
(52) U.S. Cl. ............... 709/224; 717/121; 709/219; 725/32; 455/186.1; 707/5; 715/719
(58) Field of Classification Search ......... 709/217–224, 709/200–203; 717/121; 725/32; 455/186.1; 707/5; 715/719
See application file for complete search history.

(56) References Cited

U.S. PATENT DOCUMENTS

| 5,627,766 | A | 5/1997 | Beaven |
| 6,101,500 | A | 8/2000 | Lau |
| 6,393,472 | B1 | 5/2002 | Anerousis et al. |
| 6,480,972 | B1 | 11/2002 | Cromer et al. |
| 6,587,878 | B1 | 7/2003 | Merriam |
| 6,654,816 | B1 | 11/2003 | Zaudtke et al. |
| 6,662,217 | B1 | 12/2003 | Godfrey et al. |
| 6,697,969 | B1 | 2/2004 | Merriam |
| 6,836,798 | B1 | 12/2004 | Adams |
| 7,103,874 | B2 * | 9/2006 | McCollum et al. .......... 717/121 |
| 7,289,862 | B2 | 10/2007 | Britton |
| 2003/0009553 | A1 | 1/2003 | Benfield |
| 2003/0046396 | A1 * | 3/2003 | Richter et al. ............... 709/226 |
| 2003/0055882 | A1 | 3/2003 | Kawamura |
| 2003/0063571 | A1 | 4/2003 | Ikeda et al. |
| 2004/0111638 | A1 | 6/2004 | Yadav et al. |
| 2005/0015624 | A1 * | 1/2005 | Ginter et al. ................ 713/201 |
| 2005/0086502 | A1 | 4/2005 | Rayes et al. |

OTHER PUBLICATIONS

M. Cheikhrouhou, Intelligent Agents for Network Management: Fault Detection Experiment, Corporate Communication Department, Institut Eurecom, Jul. 15, 1998, pp. 1-14, Cedex, France.
Akhil Sahai, Towards Distributed and Dynamic Network Management, INRIA-IRISA, 1998, pp. 1-10, Cedex France, Dec. 31, 1998.

* cited by examiner

Primary Examiner—Haresh N Patel
(74) Attorney, Agent, or Firm—Amin, Turocy & Calvin, LLP

(57) ABSTRACT

The present invention leverages a data gathering service to provide information regarding a system's health state via a computing entity, local and/or remote. This provides an optimized means to aggregate a single network's data and/or multiple networks' data, decreasing the amount of effort required by system administrators to manage health related alerts. In one instance of the present invention, a data gathering service aggregates health data from systems and provides access to this information via a communication means. In another instance of the present invention, aggregated, averaged data is utilized to provide manual and/or automatic control and/or management facilitation of health monitoring related tasks.

25 Claims, 46 Drawing Sheets

2600

Create Your Small Business Server Activity Report

◉ Show basic activity report (Web and e-mail)
○ Show detailed activity report (Web, e-mail, remote connections and fax)

Time Range

From: 10/28/2002 ▼

To: 11/11/2002 ▼

Create Report

E-mail Sent

| User Name | Internal E-mail | MB | External E-mail | MB | Total E-mail Sent ▼ | MB |
|---|---|---|---|---|---|---|
| Derick Namgreb | 150 | 3 | 150 | 16.2 | 300 | 19.2 |
| John Howard | 60 | 42.4 | 18 | 455.6 | 78 | 498 |
| Company Total | 210 | 45.4 | 168 | 471.8 | 378 | 517.2 |

E-mail Received

| User Name | Internal E-mail | MB | External E-mail | MB | Total E-mail Received ▼ | MB |
|---|---|---|---|---|---|---|
| Derick Namgreb | 25 | 3 | 75 | 16.2 | 100 | 19.2 |
| John Howard | 30 | 42.4 | 48 | 455.6 | 78 | 498 |
| Company Total | 55 | 45.4 | 123 | 471.8 | 178 | 517.2 |

Mailbox Size

| User Name | Starting Size (MB) | Ending Size (MB) | Rate of Change ▼ |
|---|---|---|---|
| Derick Namgreb | 25 | 75 | 200% |
| John Howard | 30 | 48 | 60% |
| Company Total | 55 | 123 | 124% |

Faxes Sent

| To | Total Faxes | Average Size (Pages) | Average Time | Average Faxes Sent per Day ▼ |
|---|---|---|---|---|
| 425.457.7771 | 32 | 2.3 | 00:01:34 | 1.1 |
| 425.452.2323 | 24 | 4.6 | 00:02:54 | 0.8 |
| Company Total | 56 | 3.4 | 00:02:01 | 1.9 |

Faxes Received

| From | Total Faxes | Average Size (Pages) | Average Time | Average Faxes Received per Day ▼ |
|---|---|---|---|---|
| 425.457.7771 | 32 | 2.3 | 00:01:34 | 1.1 |
| 425.452.2323 | 24 | 4.6 | 00:02:54 | 0.8 |
| Company Total | 56 | 3.4 | 00:02:01 | 1.9 |

Faxes Sent by User

| To | Total Faxes | Average Size (Pages) | Average Time | Average Faxes Sent per Day ▼ |
|---|---|---|---|---|
| Sally Worker | 32 | 2.3 | 00:01:34 | 1.1 |
| Mary PowerUser | 24 | 4.6 | 00:02:54 | 0.8 |
| Company Total | 56 | 3.4 | 00:02:01 | 1.9 |

Fax Traffic by Hour

| Hour ▼ | Total Faxes | Average Faxes per Day |
|---|---|---|
| 8:00 AM - 9:00 AM | 5 | 0.2 |
| 9:00 AM - 10:00 AM | 10 | 0.3 |
| 10:00 AM - 11:00 AM | 10 | 0.3 |
| 11:00 AM - 12:00 PM | 1 | 0.1 |
| 12:00 PM - 1:00 PM | 20 | 0.7 |
| 1:00 PM - 2:00 PM | 0 | 0.0 |
| 2:00 PM - 3:00 PM | 0 | 0.0 |
| 3:00 PM - 4:00 PM | 10 | 0.3 |
| 4:00 PM - 5:00 PM | 0 | 0.0 |
| Total from 8:00 AM - 5:00 PM | 56 | 1.8 |

Shared Document Usage by User

| User Name | Documents Accessed | Average Documents Accessed per Day |
|---|---|---|
| John Howard | 24 | 0.8 |
| Company Total | 56 | 1.9 |

Shared Document Usage

| Document Name | Times Accessed | Average Access per Day |
|---|---|---|
| budget.xls | 24 | 0.8 |
| Company Total | 56 | 1.9 |

Web Activity by Computer

| Computer Name | Total Active Hours | Average Active Hours per Day |
|---|---|---|
| Computer_01 | 300 | 10 |
| Computer_02 | 155 | 5.2 |
| Company Total | 455 | 15.2 |

Web Traffic by Hour

| Hour | Total Connections | Average Connections per Day |
|---|---|---|
| 8:00 AM - 9:00 AM | 200 | 6.7 |
| 9:00 AM - 10:00 AM | 100 | 3.3 |
| 10:00 AM - 11:00 AM | 50 | 1.7 |
| 11:00 AM - 12:00 PM | 1 | 0.1 |
| 12:00 PM - 1:00 PM | 100 | 3.3 |
| 1:00 PM - 2:00 PM | 1 | 0.1 |
| 2:00 PM - 3:00 PM | 1 | 0.1 |
| 3:00 PM - 4:00 PM | 1 | 0.1 |
| 4:00 PM - 5:00 PM | 1 | 0.1 |
| Total from 8:00 AM - 5:00 PM | 455 | 15.2 |

Outlook Web Access Activity by User

| User Name | Visits |
|---|---|
| | Average Visits per Day |
| Derick Namgreb | 30 | 1 |
| John Howard | 15 | 0.5 |
| Company Total | 45 | 1.5 |

Outlook Web Access Usage by Hour

| Hour | Total Visits | Average Visits per Day |
|---|---|---|
| 8:00 AM - 9:00 AM | 20 | 0.6 |
| 9:00 AM - 10:00 AM | 10 | 0.3 |
| 10:00 AM - 11:00 AM | 0 | 0 |
| 11:00 AM - 12:00 PM | 0 | 0 |
| 12:00 PM - 1:00 PM | 0 | 0 |
| 1:00 PM - 2:00 PM | 0 | 0 |
| 2:00 PM - 3:00 PM | 0 | 0 |
| 3:00 PM - 4:00 PM | 0 | 0 |
| 4:00 PM - 5:00 PM | 15 | 0.5 |
| Total from 8:00 AM - 5:00 PM | 45 | 1.5 |

Remote Connection Activity by User

| User Name | Total Connections | Average Time | Average Connections per Day |
|---|---|---|---|
| Alan Billharz | 3 | 02:34:56 | 0.2 |
| Alex Hinrichs | 2 | 00:01:22 | 0.1 |
| Alp Onalan | 2 | 00:07:49 | 0.1 |
| Charles Anthe | 4 | 00:05:17 | 0.3 |
| Company Total | 56 | 00:19:13 | 3.7 |

Remote Connection Activity by Hour

| Hour | Total Connections | Average Connections per Day |
|---|---|---|
| 8:00 AM - 9:00 AM | 20 | 0.6 |
| 9:00 AM - 10:00 AM | 10 | 0.3 |
| 10:00 AM - 11:00 AM | 0 | 0 |
| 11:00 AM - 12:00 PM | 0 | 0 |
| 12:00 PM - 1:00 PM | 0 | 0 |
| 1:00 PM - 2:00 PM | 0 | 0 |
| 2:00 PM - 3:00 PM | 0 | 0 |
| 3:00 PM - 4:00 PM | 0 | 0 |
| 4:00 PM - 5:00 PM | 15 | 0.5 |
| Total from 8:00 AM - 5:00 PM | 45 | 1.5 |

Server Specifications

Operating System: Windows .NET Server 2003 Service Pack 1

Processor: Intel(R) Pentium(R) III processor

Frequency: 498 MHz

Amount of RAM: 512 MB

**Summary for *ServerName***

Server has been running: 8 days and 12 hours

| | | |
|---|---|---|
| | Server Specifications | Details |
| | Performance Summary | Details |
| | Top Processes | Details |
| ⊗ | Backup: failed | Details |
| ⊗ | Auto-started Services Not Running: 1 | Details |
| ⊗ | Critical Alerts: 12 | Details |
| ⊗ | Critical Errors in the Event Logs: 18 | Details |

Performance Summary

| Performance Counters | Today | Last Month | Rate of Growth |
|---|---|---|---|
| Memory in use | 220 MB | 210 MB | 2% |
| Free disk space (C:) | 1,262 MB | 1,262 MB | 4% |
| Free disk space (D:) | 26,999 MB | 26,999 MB | 3% |
| Free disk space (E:) | 15,000 MB | 15,000 MB | 2% |
| Busy disk time (0 C: D: E:) | 45% | 45% | 20% |
| CPU use (0) | 22% | 11% | 100% |

Top 5 Processes by Memory Usage

| Process Name - ID | Memory Usage |
|---|---|
| lsass - 528 | 225 MB |
| STORE - 2664 | 178 MB |
| sqlservr - 2080 | 88 MB |
| inetinfo - 1608 | 70 MB |
| services - 516 | 41 MB |

Top 5 Processes by CPU Usage

| Process Name - ID | CPU Time |
|---|---|
| lsass - 528 | 16.0 % |
| STORE - 2664 | 12.7 % |
| sqlservr - 2080 | 6.3 % |
| inetinfo - 1608 | 5.0 % |
| services - 516 | 2.9 % |

Auto-started Services Not Running

| Service Name |
|---|
| Microsoft Exchange IMAP4 |
| Microsoft Exchange Information Store |
| Microsoft Exchange MTA Stacks |
| Microsoft Exchange POP3 |
| Microsoft Exchange Routing Engine |

✪ Total auto-started services not running: 5

In normal conditions, these services should be running. For details, it is recommended that you review errors in the Event log related to the service.

Critical Alerts

| Issue | Last Occurrence | Total Occurrences |
|---|---|---|
| ⊘ Low Memory | 6/16/2002, 05:59 AM | 5 |
| Low available memory may significantly decrease server performance and prevent applications from running properly. | | |
| Recommended State: At least 20 MB<br>Current State: 5.7 MB | | |

| Issue | Last Occurrence | Total Occurrences |
|---|---|---|
| ⊘ Low Free Disk space | 6/16/2002, 02:59 AM | 3 |
| Low free disk space may significantly decrease server performance and prevent applications from running properly. | | |
| Recommended State: At least 20 MB<br>Current State: 5.7 MB | | |

Critical Errors in Application Log

| Source | Event ID | Last Occurrence | Total Occurrences |
|---|---|---|---|
| ⊘ Microsoft Fax | 32012 | 6/16/2002, 02:59 AM | 79 * |
| The attempt to send the fax failed. There was no answer. This fax will not be sent, because the maximum number of retries has been exhausted. Sender: name. Billing code: password. Sender company: company. Sender dept: Department. Recipient name: . Recipient number: 7743948. Device name: Courier V.Everything EXT PnP (V90-x2). | | | |

| Source | Event ID | Last Occurrence | Total Occurrences |
|---|---|---|---|
| ⊘ MS Exchange SA | 9175 | 6/16/2002, 03:59 AM | 54* |
| The attempt to send the fax failed. There was no answer. This fax will not be sent, because the maximum number of retries has been exhausted. Sender: name. Billing code: password. Sender company: company. Sender dept: Department. Recipient name: . Recipient number: 7743948. Device name: Courier V.Everything EXT PnP (V90-x2). | | | |

SYSTEMS AND METHODS FOR HEALTH MONITOR ALERT MANAGEMENT FOR NETWORKED SYSTEMS

TECHNICAL FIELD

The present invention relates generally to network administration and control, and more particularly to systems and methods for providing health monitor alert management and control for networked systems.

BACKGROUND OF THE INVENTION

Computers were developed to aid people with repetitive tasks that were deemed to be extremely time consuming. Most of the early computers were used for complex mathematical problem solving. The first computing machines were extremely large compared to computers utilized today. Despite their enormous size, the early machines had vastly less computing power than today's machines. The sizes of computing devices were typically driven by the sizes of the existing electronic components of that era. This meant that only large research facilities or big businesses could employ computing machines. As new technology allowed for smaller electronic devices to be developed, computing devices also diminished in size. Although still lacking in power by today's standards, the size of the computing machine was reduced enough that it could be placed on a typical desk. Thus, the "desktop computer" was born. This allowed users to have computing technology available in locations other than a central computing building. People found that having the capability to utilize computing technology at their work desk, rather than submitting computing problems to a central location, made them much more productive at their jobs. To make these remotely located computers more accessible, connections were made between the computers to form "networks." This allowed a greater exchange of information from one computing location to another, and, in some cases, effectively creating one large computing system. Eventually, the idea of moving the desktop computer to the home environment to provide even more convenience for doing work became a reality and networks were extended to include these and other "offsite" locations as well.

With the advent of Internet applications, computing system requirements and demands increased dramatically. Many businesses, for example, have made important investments relating to Internet technology to support growing electronic businesses such as e-commerce. Since companies are relying on an ever increasing amount of network commerce to support their businesses, computing systems generally have become more complex in order to ensure that servers providing network services never fail. Consequently, system reliability, usage, and management are important aspects to the modern business model. These aspects are generally heightened, especially with small businesses which must control overages and waste tightly in order to remain competitive in tight markets.

A first approach for providing powerful and reliable services utilized a large multiprocessor system (e.g., mainframe) for managing servers, for example. Since more than one processor may be involved within a large system, services can continue even if one of a plurality of processors fails. Unfortunately, these large systems can also be extraordinarily expensive and available to only the largest of corporations. A second approach for providing services involves employing a plurality of lesser expensive systems (e.g., off-the-shelf personal computers) individually configured as an array to support a desired service. Although these systems can provide a more economical hardware solution, system management and administration of individual servers is generally more complex and time consuming.

Currently, management of a plurality of servers is a time-intensive and problematic endeavor. For example, managing server content (e.g., software, configuration, data files, components, etc.) requires administrators to explicitly distribute (e.g., manually and/or through custom script files) new or updated content and/or configurations (e.g., web server configuration, network settings, etc.) across the servers. If a server's content becomes corrupted, an administrator often has no automatic means of correcting the problem. Furthermore, configuration, load-balance adjusting/load balance tool selection, and monitoring generally must be achieved via separate applications. Thus, management of an entity (e.g., a plurality of computers acting collectively) as a whole, generally requires individual configuration of loosely coupled services that inherently increases errors and time expenditure.

The problems are often compounded when usage of the system includes resource utilization that is outside the scope of normal business activity. This taxes the resources of the system and reduces profitability of businesses. Some examples of this type of activity include, personal emails, web "surfing," and network gaming and the like that are counter to a business' goals. Thus, administrators are not only tasked with keeping a network system up and running, they may also be required to assist the business with fine tuning usage of the network itself. This requires information beyond what is typically available to a system administrator. This problem is compounded by the fact that most small businesses cannot afford to have their own system administrators "in house." Therefore, most activities are performed from a remote location by a provider who may also be servicing many other network systems for other businesses. Thus, the amount of information required to efficiently perform normal health monitoring and statusing of multi-systems becomes an overwhelming task, especially if a business also expects facilitation with improving a system's utilization.

SUMMARY OF THE INVENTION

The following presents a simplified summary of the invention in order to provide a basic understanding of some aspects of the invention. This summary is not an extensive overview of the invention. It is not intended to identify key/critical elements of the invention or to delineate the scope of the invention. Its sole purpose is to present some concepts of the invention in a simplified form as a prelude to the more detailed description that is presented later.

The present invention relates generally to network administration and control, and more particularly to systems and methods for providing health monitor alert management and control for networked systems. A data gathering service is leveraged to provide information regarding a system's health state via a computing entity, local and/or remote. This provides an optimized means to aggregate a single network's data and/or multiple networks' data, decreasing the amount of effort required by system administrators to manage health related alerts. By providing customizable aggregated health data, an administrator can efficiently maintain more networks in substantially the same amount of time it took to previously manage a substantially smaller amount of networks. The administrator also gains an ability to provide health related system state information to a customer that requests network-related health data. In one instance of the present invention, a data gathering service aggregates health data from systems administered by the administrator and provides access to this information via a communication means, such as the Internet, for example. This permits administrators to interface with pertinent information virtually anywhere they can find access to the communication means. Thus, the present invention vastly improves administrative productivity while enhancing the utilization of systems being administered to. In another instance of the present invention, aggregated, averaged data is utilized to provide manual and/or automatic control and/or management facilitation of health monitoring related tasks.

To the accomplishment of the foregoing and related ends, certain illustrative aspects of the invention are described herein in connection with the following description and the annexed drawings. These aspects are indicative, however, of but a few of the various ways in which the principles of the invention may be employed, and the present invention is intended to include all such aspects and their equivalents. Other advantages and novel features of the invention may become apparent from the following detailed description of the invention when considered in conjunction with the drawings.

BRIEF DESCRIPTION OF THE DRAWINGS

FIG. 31 is a screen shot of an activity report user interface in accordance with an aspect of the present invention.

FIG. 32 is a screen shot of an e-mail utilization report user interface in accordance with an aspect of the present invention.

FIG. 33 is a screen shot of a fax utilization report user interface in accordance with an aspect of the present invention.

FIG. 34 is a screen shot of a document utilization report user interface in accordance with an aspect of the present invention.

FIG. 35 is a screen shot of a web utilization report user interface in accordance with an aspect of the present invention.

FIG. 36 is a screen shot of a web access utilization report user interface in accordance with an aspect of the present invention.

FIG. 37 is a screen shot of a remote connection utilization report user interface in accordance with an aspect of the present invention.

FIG. 38 is a screen shot of a remote user portal user interface in accordance with an aspect of the present invention.

FIG. 40 is a screen shot of an overall server summary performance report user interface in accordance with an aspect of the present invention.

FIG. 41 is a screen shot of a performance summary report user interface in accordance with an aspect of the present invention.

FIG. 42 is a screen shot of a Top 5 performance parameter report user interface in accordance with an aspect of the present invention.

FIG. 43 is a screen shot of a service failure report user interface in accordance with an aspect of the present invention.

FIG. 44 is a screen shot of a critical alert and log errors report user interface in accordance with an aspect of the present invention.

DETAILED DESCRIPTION OF THE INVENTION

Figure 1:
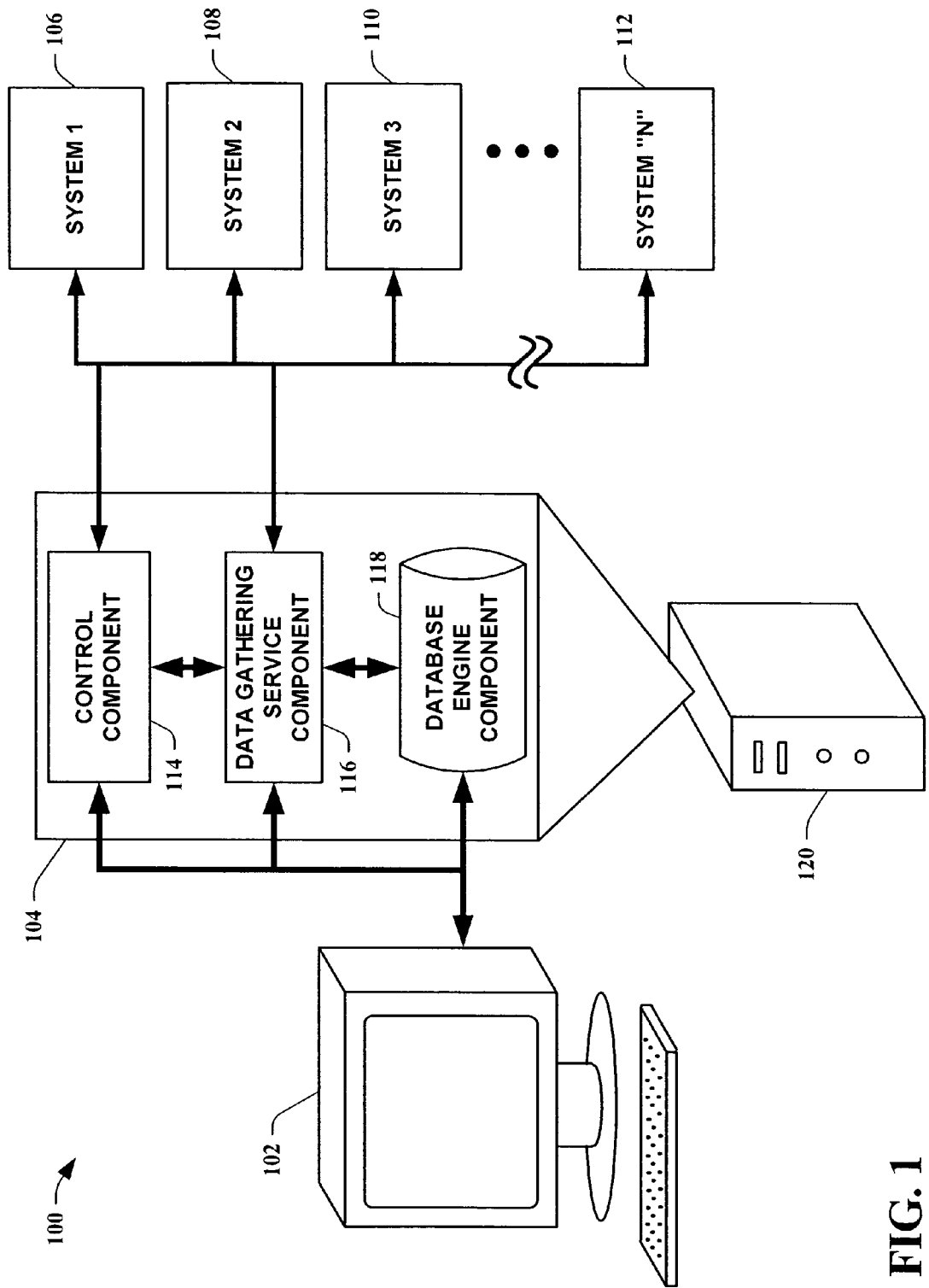
FIG. 1 is a block diagram of an information and control system in accordance with an aspect of the present invention.

The present invention is now described with reference to the drawings, wherein like reference numerals are used to refer to like elements throughout. In the following description, for purposes of explanation, numerous specific details are set forth in order to provide a thorough understanding of the present invention. It may be evident, however, that the present invention may be practiced without these specific details. In other instances, well-known structures and devices are shown in block diagram form in order to facilitate describing the present invention.

As used in this application, the term "component" is intended to refer to a computer-related entity, either hardware, a combination of hardware and software, software, or software in execution. For example, a component may be, but is not limited to being, a process running on a processor, a processor, an object, an executable, a thread of execution, a service, a program, and/or a computer. By way of illustration, both an application running on a server and the server can be a computer component. One or more components may reside within a process and/or thread of execution, and a component may be localized on one computer and/or distributed between two or more computers. A "thread" is the entity within a process that the operating system kernel schedules for execution. As is well known in the art, each thread has an associated "context" which is the volatile data associated with the execution of the thread. A thread's context includes the contents of system registers and the virtual address belonging to the thread's process. Thus, the actual data comprising a thread's context varies as it executes. A "state" of a networked system refers to a condition of the networked system in relation to, but not limited to, performance, health, and usage parameters. A state can be a snapshot of a system's status relating to an historical instance in time and/or to a current instance in time and/or a future instance in time.

In FIG. 1, a block diagram of an information and control system 100 in accordance with an aspect of the present invention is shown. The information and control system (I&C system) 100 is comprised of a user interface 102, a system service component 104, and monitored and controlled systems 106-112. The user interface 102 can be any type of interfacing device and/or method that relays and/or accepts information from a user and/or entity. Thus, the user interface 102 can be a graphical user interface and/or a text based interface and the like. It 102 can also include input devices such as a keyboard, mouse, pen, touch screen, and/or environmental awareness inputs. The input devices can also include serial ports, buses, and other signal input devices and the like. The user interface 102 interfaces with the system service component 104. The system service component 104 is comprised of a control component 114, a data gathering service component 116, and a database engine component 118. The system service component 104 can reside on a computing system such as a server 120 and the like. It 104 can also reside on a desktop computing system and/or on distributed computing systems and/or a central computing system. Thus, the system service component 104 can reside remotely to a system administrator and/or remotely to a system being administered to. It is also within the scope of the present invention that various sub-components of the system service component 104 can reside in a distributed manner. The system service component 104 interfaces with the user interface 102 and the systems 106-112. The control component 114 provides control of the systems 106-112 by the user interface 102 and/or the data gathering service component 116 and/or another controlling entity (not shown) such as a computing entity and the like, located locally and/or remotely. The control component 114 can also be structured to provide predetermined control with no or minimum prompting by external entities. In other instances of the present invention, the control component 114 is part of the data gathering service component 116. Likewise, it 114 can also be part of the user interface 102. The data gathering service component 116 provides information relating to the systems 106-112 to a database system such as that provided by the database engine component 118. The database engine component 118 can be comprised of any type of database engine, distributed and/or integrated. Each of the systems 106-112 is typically comprised of networks owned by a particular client or company, for example. System "N" 112 represents the "nth" system in any number of systems from 1 to infinity. However, ownership is not necessarily a definitive element for defining a system. Furthermore, the systems 106-112 can be comprised of a single computing device or multiple networked computing devices in a substantially similar location and/or in a substantially different location. Thus, even a remotely located computing device can still be considered part of a system if so desired. A system can also be comprised of a single network and/or multiple networks and/or multiple sub-networks and combinations thereof.

Generally speaking, the systems 106-112 generate health, performance, usage, and other data that enables an administrative agent to monitor, control, and report different aspects of the systems 106-112. Owners of these systems 106-112 are usually small businesses that hire an administrative agent to set up, maintain, and control their system. The administrative agent, who is generally in business to provide these services, must also provide similar services to other customers. Thus, the administrative agent typically oversees multiple systems owned by multiple clients at a remote location to the systems. This creates a huge influx of information that must be assessed by the administrative agent. In one aspect of the present invention, the data gathering service component 116 aggregates system information such as health, usage, and performance information and stores it in the database engine component 118. This permits the administrative agent to access the information and generate aggregated reports. This substantially cuts down on the amount of information that must be assessed by the administrative agent. It also permits trends and patterns of system errors to be tracked not only on a single system but over multiple systems to possibly permit prediction of common mode failures/errors of a common piece of hardware for instance. Historical time-based trends can also be tracked. This permits a system utilizing the present invention to provide historical, computer network, and/or multi-site data mining. System reports provided by access to the aggregated data permits control responses to be initiated manually by the administrative agent and/or automatically by the control component 114. The automatic responses can be default responses and/or programmed responses by the administrative agent. Thus, if a particular user of a system is over utilizing an internet bandwidth connection, the present invention provides a means to respond to reduce that particular utilization. This permits a case-by-case assessment without requiring a system-wide mandate to curb a particular system asset. Control can be accomplished for such assets as e-mail, internet access, faxing, CPU utilization, and the like. For example, reports regarding a particular user's send and receive habits can be generated and provided to a client. This adds value to an administrative agent's business. It also provides value to the system's owner who can utilize the reports to determine productivity of individual users of the system.

By utilizing the aggregated data, the present invention can also reduce faulty or "noise" errors. A system employing the present invention can connect to a service that updates/predicts/assists with known bugs/noise errors, and this information can be reported to an administrator of the system and/or automatically incorporated as adjusted threshold alert values and/or changes to a system's state such as updating system software and the like to prevent any further bogus errors from occurring. The aggregated data can also be incorporated into a learning system employing artificial intelligence (AI) to predict and/or pattern a system into a more productive model. A system, such as an AI system, employing the present invention can also be utilized to perform management tasks to increase productivity of end-users of the system through employment of aggregated utilization information.

Figure 2:
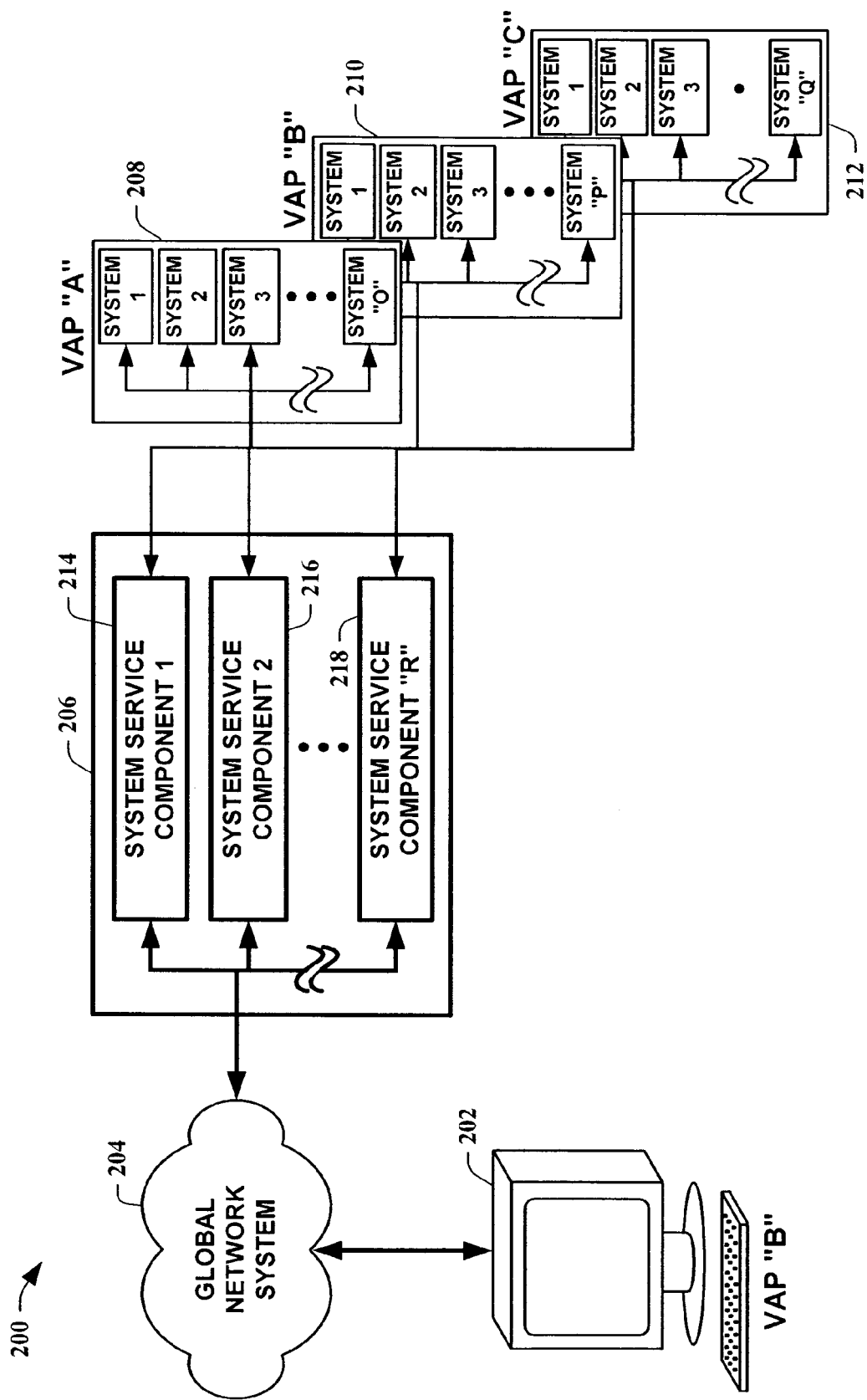
FIG. 2 is another block diagram of an information and control system in accordance with an aspect of the present invention.

Turning to FIG. 2, another block diagram of an information and control system 200 in accordance with an aspect of the present invention is illustrated. The information and control system (I&C system) 200 is comprised of a user interface 202, a communication means 204, a servicing center component 206, and various system groupings 208-212. The user interface 202 can be any type of interfacing device and/or method that relays and/or accepts information from a user and/or entity. Thus, the user interface 202 can be a graphical user interface and/or a text based interface and the like. It 202 can also include input devices such as a keyboard, mouse, pen, touch screen, and/or environmental awareness inputs. The input devices can also include serial ports, buses, and other signal input devices and the like. The user interface 202 interfaces with the servicing center component 206 via the communication means 204. The communication means 204 can include, but is not limited to, a global network system such as the Internet for example, a LAN network communication means, a WAN network communication means, and other communication means accomplished via signal such as telecommunications, satellite communications, radio communications and the like. The servicing center component 206 is comprised of system service component 1 214, system service component 2 216, and system service component R 218, where R represents any number from 1 to infinity. The servicing center component 106 interfaces with the various system groupings 208-212. The various system groupings 208-212 are representative of a grouping of systems that represent any number of systems from 1 to infinity. System grouping VAP "A" 208 is comprised of multiple systems from 1 to "O," where "O" represents any number from 1 to infinity. "VAP" is an acronym for "value-added provider" and is typically representative of a for-hire system administrator who monitors multiple systems for different clients. In this example, the individual systems under VAP "A" represent different systems for different clients that have an agreement with the same value-added provider, VAP "A." System grouping VAP "B" 210 is comprised of multiple systems from 1 to "P," where "P" represents any number from 1 to infinity. In this example, the individual systems under VAP "B" represent different systems for different clients that have an agreement with the same value-added provider, VAP "B." System grouping VAP "C" 212 is comprised of multiple systems from 1 to "Q," where "Q" represents any number from 1 to infinity. In this example, the individual systems under VAP "C" represent different systems for different clients that have an agreement with the same value-added provider, VAP "C."

The servicing center component 206 provides a central entity that services multiple VAPs by aggregating information and/or providing control of systems administered by those VAPs. Thus, system service component 1 214 aggregates information and/or provides control of systems administered by VAP "A." System service component 2 216 aggregates information and/or provides control of systems administered by VAP "B." Likewise, system service component "R" 218 aggregates information and/or provides control of system administered by VAP "C." Although only three sets of VAP systems are shown, one skilled in the art can appreciate that there can be any number of VAP system groupings from 1 to infinity. There also can be system overlapping such as when a client has multiple VAPs overseeing various aspects of a single and/or multiple networks within the client's organization. In this example of an instance of the present invention, the user interface 202 represents an interface for VAP "B." VAP B is chosen only for illustrative purposes. The user interface 202 can be an interface for any VAP and/or multiple VAPs. The servicing center component 206 provides the service component 2 216 to administer data aggregation and/or control of VAP B's clients (i.e., networks and the like). This alleviates VAP B of the requirement of having equipment that can process and handle the throughput of all of their clients' system data. The data aggregation and/or control is provided by the system service component 2 216, along with any CPU and/or resources required to process the data and/or provide control. This permits VAP B to access system service component 2 216 via the communication means 204 at any remote location serviced by the communication means 204. Thus, this instance of the present invention provides relief of asset possession and relief of limited accessibility of information and/or control by a VAP, minimizing the workload of the VAP. The servicing center component 206 additionally has the ability to cross-compare various systems for making a determination if an error, such as a hardware error, for example, is a common mode error/failure pertinent to a particular entity that may be found in multiple systems. This allows the servicing center 206 to notify VAPs of a potential for common errors/failures with regard to a particular entity such as common software and/or hardware entities and the like. It also permits erroneous errors and/or software bugs to be eliminated through filtering and/or software updates, accomplished manually and/or automatically.

Figure 3:
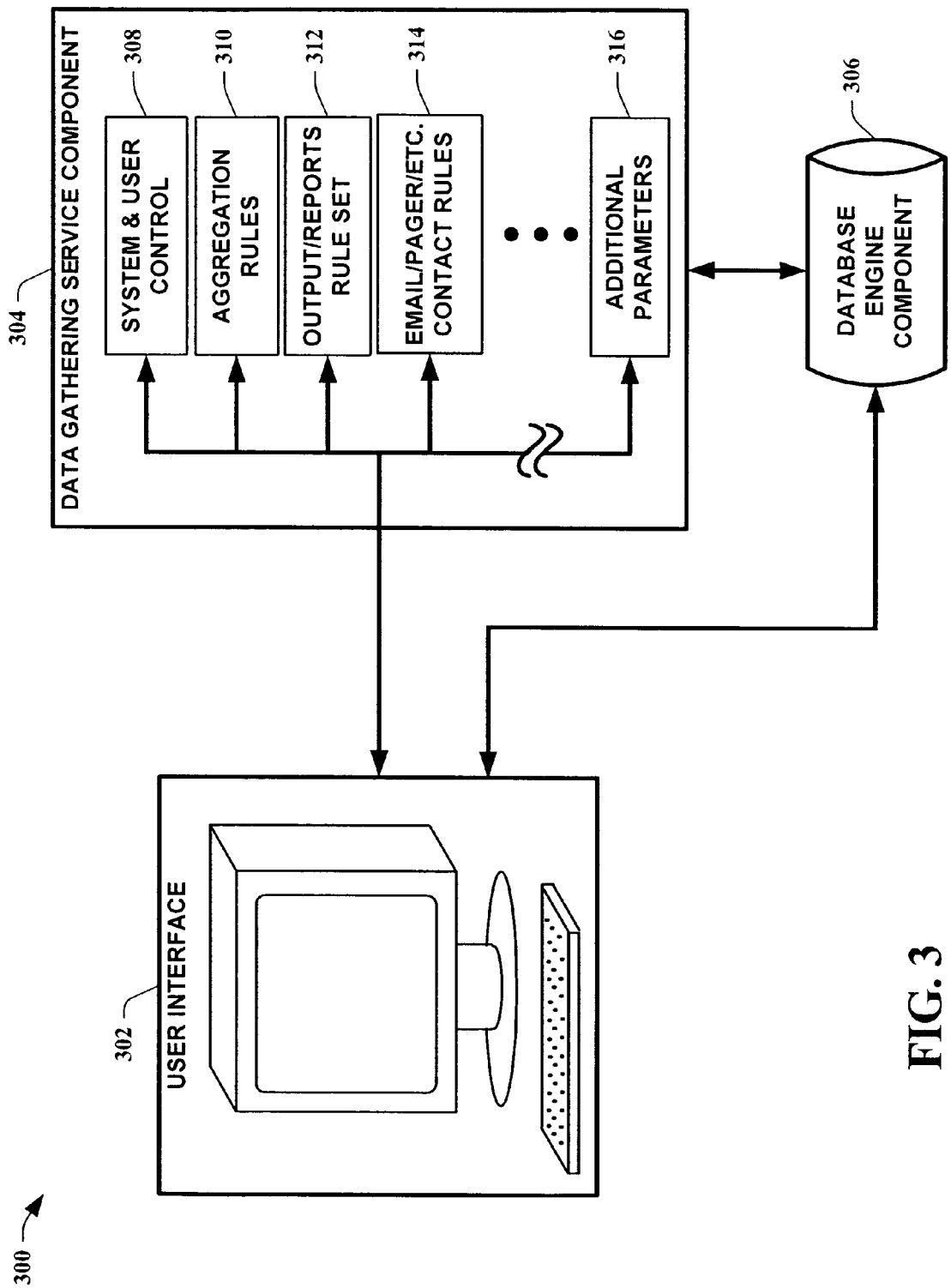
FIG. 3 is yet another block diagram of an information and control system in accordance with an aspect of the present invention.

Looking at FIG. 3, yet another block diagram of an information and control system 300 in accordance with an aspect of the present invention is depicted. The information and control system (I&C system) 300 is comprised of a user interface 302, a data gathering service component 304, and a database engine component 306. The user interface 302 can be any type of interfacing device and/or method that relays and/or accepts information from a user and/or entity. Thus, the user interface 302 can be a graphical user interface and/or a text based interface and the like. It 302 can also include input devices such as a keyboard, mouse, pen, touch screen, and/or environmental awareness inputs. The input devices can also include serial ports, buses, and other signal input devices and the like. The user interface 302 interfaces with the data gathering service component 304 and/or the database engine component 306. The data gathering service component 304 is comprised of system and user control parameters 308, aggregation rules parameters 310, output/reports rule set parameters 312, e-mail/pager/etc. contact rules parameters 314, and additional parameters 316. The system and user control parameters 308 provide manual and/or automatic control of various system parameters based upon information aggregated by the data gathering service component 304. This enables a user and/or entity to manipulate assets of a client's system in order to achieve optimal utilization of that system for its intended purpose. These parameters 308 can be set via the user interface 302 and/or utilize default values set by the data gathering service component 304 and/or by an additional entity such as an AI controlling unit. The aggregation rules parameters 310 provide a means for the data gathering service component 304 and/or the user interface 302 to control how and/or what and/or when and the like that gathered information is aggregated. This permits a powerful amount of control over administration of a system. It allows only information that is deemed of high importance to a user (e.g., value-added provider (VAP)) to be presented in an efficient manner, saving vast amounts of time and/or manual composition effort of the same information. Aggregated data will inherently have greater value than the sum of its parts due to the added benefits of showing trend data and other hidden data. Finding hidden data is often referred to as "data mining." The aggregated data provided by the present invention allows exploitation of a data set not previously obtainable. The output/reports rule set parameters 312 allow a user utilizing the user interface 302 to set rules that govern what and/or how information is presented. This allows a VAP to provide clients with an informative and detailed report that is tailored for that particular client. The e-mail/pager/etc. contact rules parameters 314 allow control of what and/or under what conditions a contact can be initiated. Thus, if a server has gone down but resets itself within 2 minutes, a user could decide that that is sufficiently within a client's tolerance level and choose not to be notified. However, the same condition that is not reconciled within 3 minutes can prompt a contact by the data gathering service component 304. This alerts a VAP to a possibly serious condition. Since the VAP can control under what circumstances they are notified, a notification can be deemed to need immediate attention by the VAP rather than the VAP being inundated with contacts for minor system problems that do not require their immediate attention. One skilled in the art can appreciate that other parameters can be utilized by the data gathering service component as represented by the additional parameters 316. Thus, the data gathering service component 304 is not limited solely by those parameters illustrated in FIG. 3. Due to the enormous value of the aggregated data, users obviously can find the information invaluable in ways that are explicitly stated and/or illustrated, but are within the scope of the present invention. Thus, the present invention allows for the flexibility of providing parameters that a user can manually manipulate and/or permit automatic manipulation based upon an aspect and/or related aspect of the aggregated data. Although not expressly shown in FIG. 3, it has been discussed supra that the data gathering service component 304 utilizes the database engine component 306 to store gathered data. This permits the user interface 302 to facilitate in generating reports and/or views of data for display/dissemination by either interfacing with the data gathering service component 304 and/or directly with the stored data in the database engine component 306.

Figure 4:
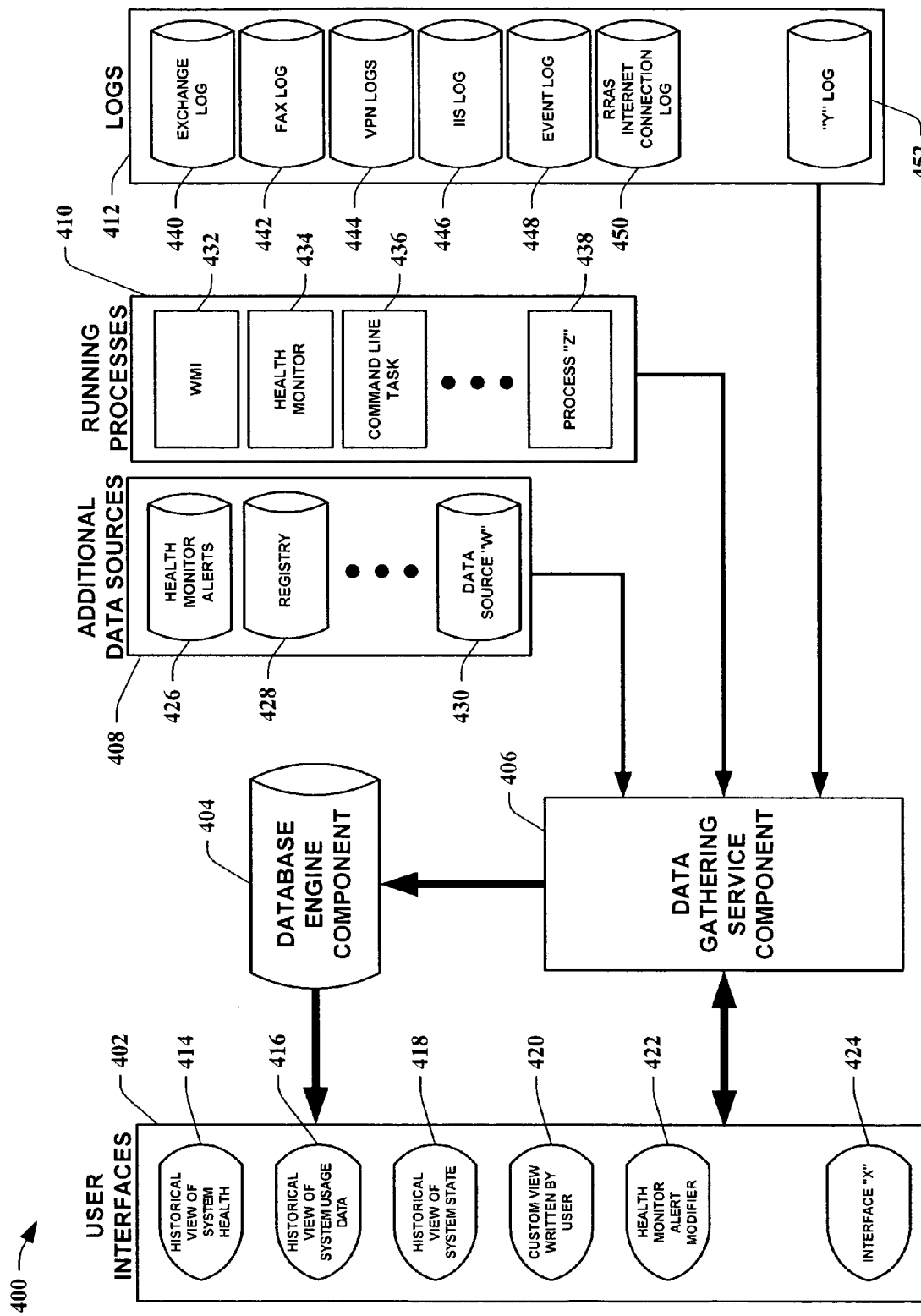
FIG. 4 is still yet another block diagram of an information and control system in accordance with an aspect of the present invention.

Referring to FIG. 4, still yet another block diagram of an information and control system 400 in accordance with an aspect of the present invention is shown. The information and control system (I&C system) 400 is comprised of user interfaces 402, database engine component 404, data gathering service component 406, additional data sources 408, running processes 410, and logs 412. The user interfaces 402 is comprised of a historical view of system health 414, a historical view of system usage data 416, historical view of system state 418, custom view written by user 420, health monitor alert modifier 422, and interface "X" 424, where X represents any number of interfaces from 1 to infinity and/or any type of interface. The user interfaces 402 interface with the database engine component 404 and/or the data gathering service component 406 to obtain data to generate various user interfaces represented by the user interfaces 402 and/or receives generated reports directly from the data gathering service component 406. The data gathering service component 406 additionally interfaces with the database engine component 404 to provide information relating to a system and/or provide generated reports to the user interfaces 402. A representative, but incomplete, example of such information that is obtainable by the data gathering service component 406 includes, but is not limited to, additional data sources 408, running processes 410, and logs 412. The additional data sources 408 is comprised of health monitor alerts 426, registry 428, and data source "W" 430, where W represents any number of data sources from 1 to infinity and/or unlimited types of data sources. The running processes 410 is comprised of WMI (Microsoft's Windows Management Instrumentation) 432, health monitor 434, command line task 436, and process "Z" 438, where Z represents any number of running processes from 1 to infinity and/or unlimited types of processes. The logs 412 are comprised of an exchange log 440, a fax log 442, VPN (Virtual Private Network) logs 444, IIS (Internet Information Server) log 446, event log 448, RRAS (Microsoft's Routing & Remote Access Service) internet connection log 450, and "Y" log 452, where Y represents any number of logs from 1 to infinity and/or unlimited types of logs.

FIG. 4 represents an example of an instance of the present invention of a single system and the types of data that the data gathering service component 406 interfaces with. These different types of data sources 408-412 are representative and not meant to be all inclusive. The data gathering service component 406 aggregates this information from at least one of the data sources 408-412. This information is then stored on the database engine component 404. The database engine component 404 can be a distributed type of database engine and reside on a server that is controlled by user such as a VAP. The user interfaces 402 can retrieve aggregated data directly from the database engine component 404 and/or the data gathering service component 406. The user interfaces 402 can additionally interface with the data gathering service component 406 to provide parameters utilized by the data gathering service component 406 in its data aggregation related tasks. These related tasks include, in this illustration, control of the system along with such tasks as system alert reporting and aggregation control.

Figure 5:
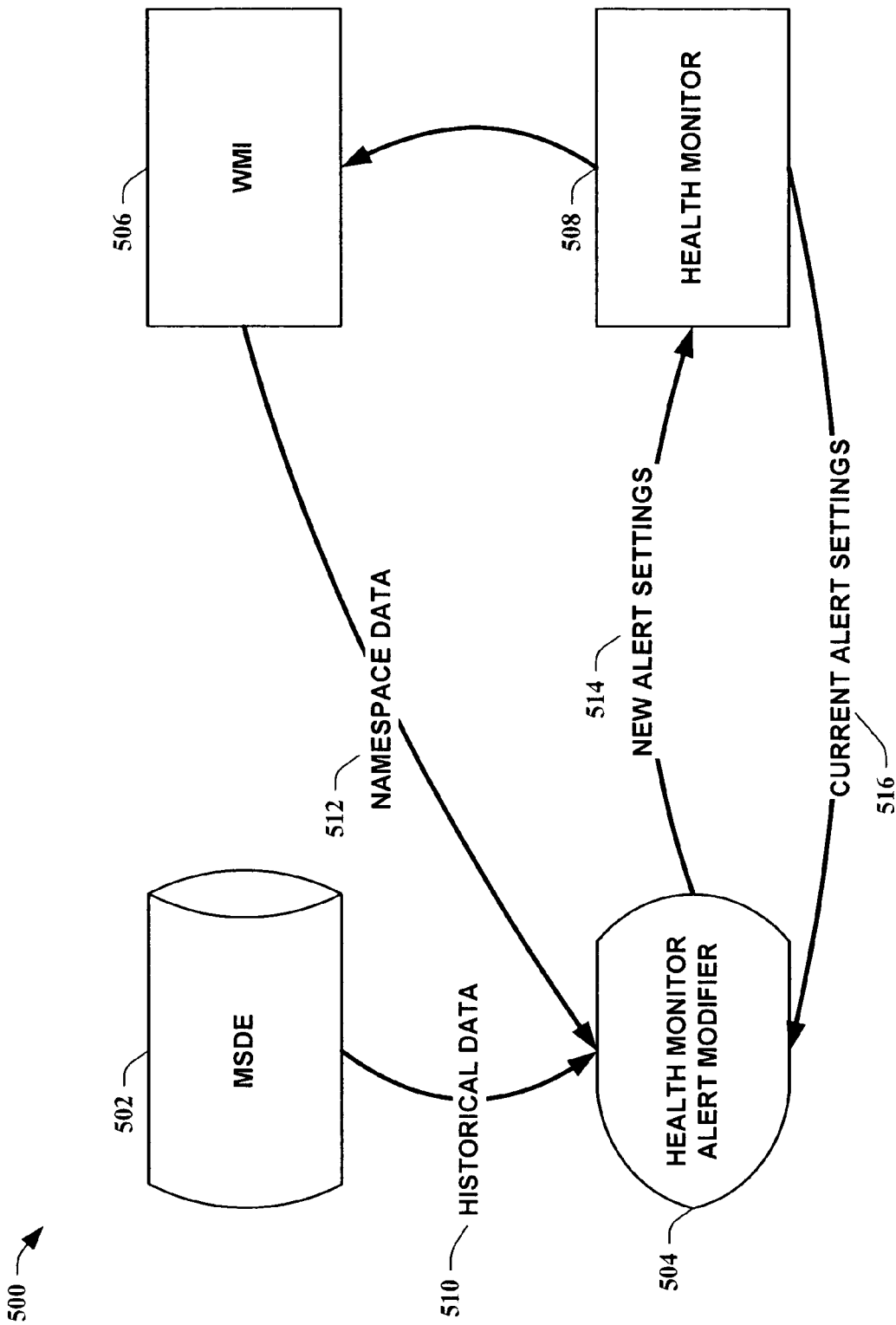
FIG. 5 is a block diagram of an information and control system utilized for controlling and setting monitoring alerts in accordance with an aspect of the present invention.

In FIG. 5, a block diagram of an information and control system 500 utilized for controlling and setting monitoring alerts in accordance with an aspect of the present invention is illustrated. The information and control system (I&C system) 500 is comprised of a database engine component 502 such as, for example, Microsoft's SQL (Structured Query Language) Server Database Engine (MSDE); a user interface 504 for providing a means to receive information and to control a process; data sources 506, such as, for example, running processes such as Microsoft's Window Management Instrumentation (WMI); and a controllable process 508 such as, for example, a health monitor process. In this example of an instance of the present invention, the I&C system 500 is utilized to monitor and set thresholds for a health monitoring process of a system. As an example illustrating data interaction, the user interface 504 interacts with the database engine component 502, the data sources 506, and the controllable process 508. The user interface 504 receives historical data 510 from the database engine component 502 that can be, for example, rolling average data relating to a health monitor process. Additional desired information such as, for example, name space data 512 such as instantaneous state of services data is obtained from the data sources 506. The user interface 504 also interacts with the controllable process 508 to obtain current alert settings 516 from the controllable process 508 and also interacts to send new alert settings 514 to the controllable process 508. In this manner, the user interface 504 can provide valuable status and alert information pertaining to a particular process in a system. As in the example of the health monitor alert modifier, health alerts and alert thresholds can be easily set, even by inexperienced system administrators, due to the I&C system 500 providing historical information and suggestions based on that historical information to facilitate in alert setting, automatically and/or manually.

A small business server environment desires robust administration tools without imposing extensive burdens and complexities on system administrators. The present invention can be incorporated in a system that provides for accumulating tailored information about the health of a server's environment and utilizing information to provide useful administrative guidance. In one instance of the present invention, the present invention provides a simplified user interface to a server environment health monitoring and alert system—providing for definition and implementation of alerts based on instantaneous measurements and time averaged data. Thus, the present invention can, for example, bring together a health monitor process and an historical system state utilizing a database engine component such as Microsoft's SQL's MSDE engine in order to provide a user a historical view of relevant data to enable a better understanding of related alerts. Furthermore, the present invention also provides a simple user interface for setting thresholds in a process such as, for example, the health monitor process. Historical data is very effective in facilitating a user to select a threshold for alerting. Each system and network runs differently, and the present invention provides a rolling average of data. Ultimately, this helps minimize frivolous alerts and time spent by a system's owner, both in setting alerts and in responding to alerts.

FIG. 5 illustrates, as an example, such a system for providing a simplified method for modifying alert thresholds in a health monitor process as well as providing control for turning on and off related alerts. Additionally, the present invention provides averaging, such as a rolling 30 day average, of data corresponding to alert thresholds. This allows a user to make informed decisions when setting the alert thresholds, since the data is based on actual system measurements.

Figure 6:
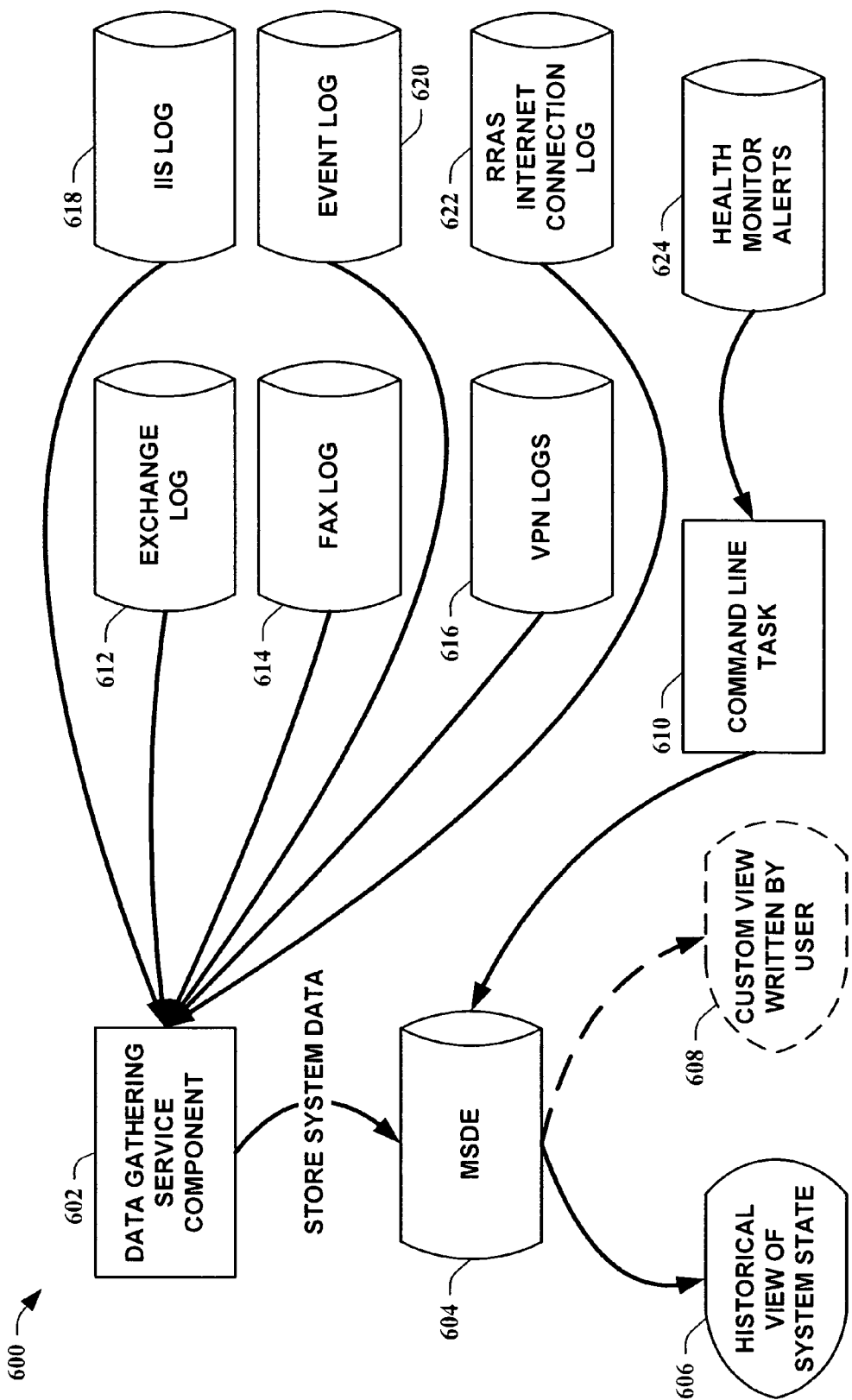
FIG. 6 is a block diagram of an information and control system utilized for gathering historical system data in accordance with an aspect of the present invention.

In order to provide information for enhancing system interaction with a user, the present invention provides a means to gather historical data that can be utilized to facilitate a user's administration of the system. In FIG. 6, a block diagram of an information and control system 600 utilized for gathering historical system data in accordance with an aspect of the present invention is shown. The I&C system 600 is comprised of a data gathering service component 602; a database engine component 604 such as Microsoft's SQL Server Database Engine; an historical user interface 606; an optional customized user interface 608; a running process 610 such as a command line task process; and various log and alert databases 612-624. The various log and alert databases are comprised of, for example, an exchange log 612, a fax log 614, VPN logs 616, an IIS log 618, an event log 620, an RRAS internet connection log 622, and a health monitor alerts database 624. The various log and alert databases 612-624 are representative examples and are not meant to be required and are not an exhaustive list of all possible log and alert databases. In this example of an instance of the present invention, the data gathering component 602 obtains information from the logs 612-622. This information is then stored utilizing the database engine component 604. The running process 610 can also provide data to the database engine component 604 from other databases such as the health monitor alerts database 624. This allows a user to access information from an interface such as the historical user interface 606. The user can also modify and/or create an interface to construct the optional customized user interface 608. This permits versatility to tailor the interface to user's desired configuration. The data gathering service component 602 can actively retrieve data from various data sources through polling and the like and/or it 602 can passively receive data transmitted by the various data sources on a periodic and/or aperiodic basis. Thus, the present invention provides a means to view and assess historical system information to facilitate in optimizing future system performance, track error events, and determine trends and the like for a given system.

The present invention can be incorporated in a system that provides for accumulating tailored information about a state of a system such as, for example, the health of a server environment and utilizes gathered information to provide useful administrative guidance. In one instance of the present invention, collection of information is facilitated by bringing together a distributed database engine such as, for example, an SQL MSDE engine and several sources of system information to provide for historical monitoring of an entire system state. System information can be collected from running processes such as, for example, a health monitor process and also collected from logged data such as, for example, an event log, an Exchange log, an IIS log, and a fax log. The system information is then inserted into a server such as, for example, an SQL server, where customized reports can be generated and provided to the customer. The present invention enables users/clients to more accurately and quickly monitor the overall health and utilization of their server and network, reducing system operating costs. It also provides for rich data mining of system data by utilizing, for example, a custom schema installed into a database engine component such as MSDE. Thus, when data is collected, it can be inserted into a structured format such as, for example, schema tables. The data can then be retrieved utilizing predefined user interfaces or "views," for example, for web viewing and e-mail reporting.

Figure 7:
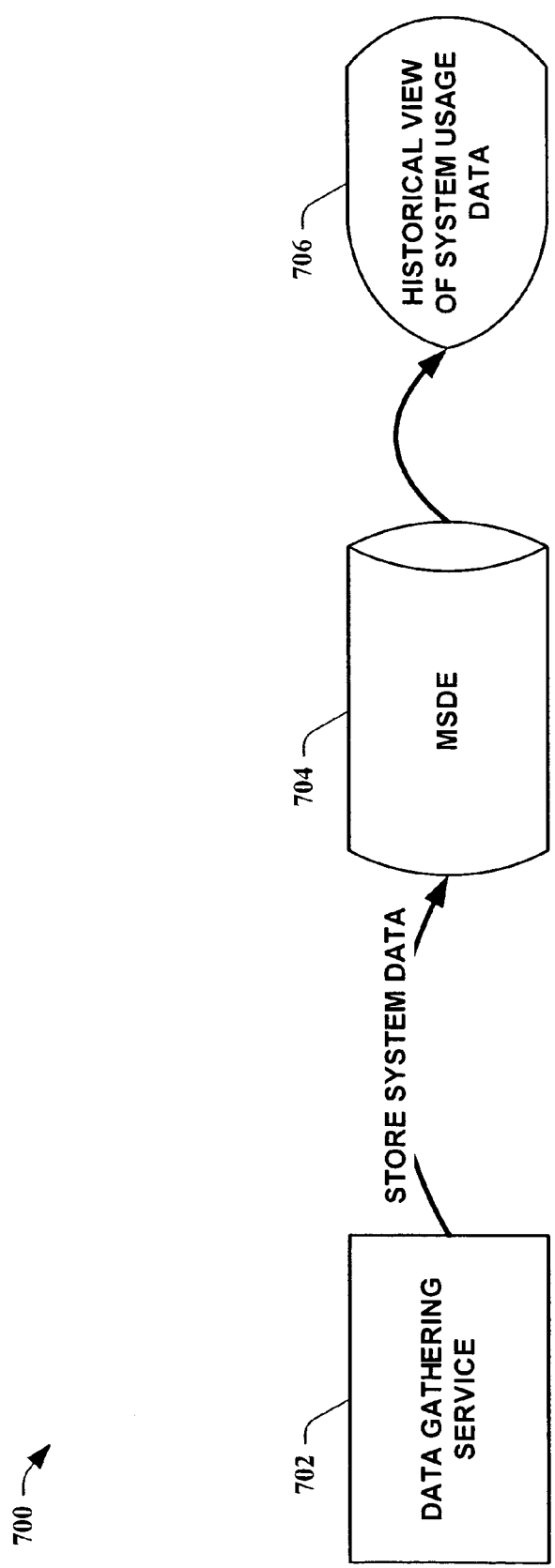
FIG. 7 is a block diagram of an information and control system utilized for providing system utilization information in accordance with an aspect of the present invention.

Another instance of the present invention provides a system administrator with periodic reports on system utilization based on user and system defined criteria and the like. The present invention brings together utilization data from a variety of administrator and system defined sources to create these reports and/or provide utilization control of the system. In FIG. 7, a block diagram of an information and control system 700 utilized for providing system utilization information in accordance with an aspect of the present invention is depicted. The I&C system 700 is comprised of a data gathering service component 702; a database engine component 704 such as, for example, Microsoft's SQL Server Database Engine; and a user interface 706 such as an historical view of system utilization data and the like. The present invention brings together historical data collection services and data storage engines such as, for example, SQL's MSDE engine, for data storage in order to present a system administrator and system owner/client a unified view of overall utilization of the system and/or utilization control of the system, reducing system costs and improving system utilization.

In a typical example of the present invention, a data collection service runs once daily and collects a wide range of system data. It then stores this set of collected information in a database engine component, viewable via a defined view of system utilization data based on the set of collected information. This view or report can be based on user input based on a wide base set of statistics the user finds useful. Providing users with this type of report saves them from having to log on to a system and pour through logs from many different sources. This ultimately saves time and money to a user's client or owner of the system. A system utilization report shows a client how their system users are interacting with their system. This provides information that a client can utilize to enhance the performance of the system and/or utilize to enhance the performance of the system's user. For example, if a particular system user or employee has a high e-mail send and/or receive usage along with hours of internet usage per day, an employer (i.e., the client) can adjust the situation directly by confronting the employee about productivity and/or the employer can inform a system's administrator (i.e., user) to restrict that particular employee's internet bandwidth and emailing capabilities. Thus, the present invention goes beyond just enhancing a system's performance, but can also be utilized to enhance the productivity and/or management of employees utilizing a client's system. Similarly, the present invention can be used to directly monitor employee activities to provide a substantially real-time monitor of their productivity. Reports and/or controlling actions can be implemented manually and/or automatically based upon the aggregated utilization data. Beyond solely monitoring employee activity, the present invention can also be utilized to actually enforce business rules based on a business owner's preferences utilizing positive feedback. For example, a business rule could require that no single employee can utilize more than 5% of available bandwidth allotted by a system administrator for non-critical utilization such as, for example, internet web browsing, This naturally enforces the business rule while protecting a networked system's bandwidth for critical applications such as, for example, system backup and/or e-mail applications.

Figure 8:
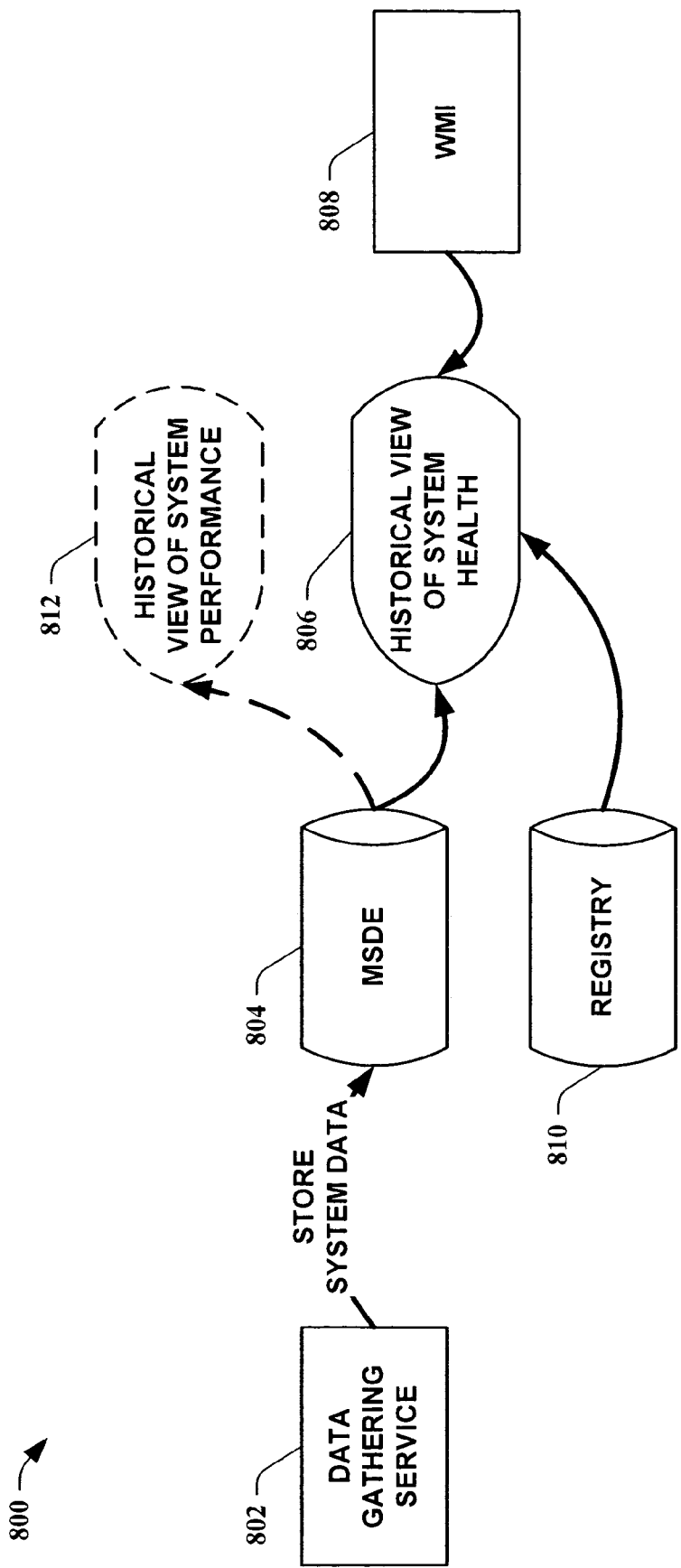
FIG. 8 is a block diagram of an information and control system utilized for providing system health and performance information in accordance with an aspect of the present invention.

Yet another instance of the present invention brings together historical data collection services and data storage engines such as, for example, an MSDE engine, for data storage in order to present a system administrator/user and system client/owner a unified view of overall health of a system. Looking at FIG. 8, a block diagram of an information and control system 800 utilized for providing system health and performance information in accordance with an aspect of the present invention is illustrated. The I&C system 800 is comprised of a data gathering service component 802; a database engine component 804 such as, for example, Microsoft's SQL Server Database Engine; a user interface 806 such as an historical view of system health and the like; an optional user interfaces such as, for example, an historical view of system performance and the like 812; additional database 810 such as, for example, a system registry; and a running process 808 such as, for example, Microsoft's Windows Management Instrumentation.

In one instance of the present invention, a data collection service runs once per hour and collects a wide range of system health and/or performance data. It then stores this collected set of information in a database engine component such as an MSDE store. The present invention provides a user/administrator with a view/interface of system health and performance data utilizing the set of collected information. Based on customer input and/or system defaults, a system health and performance report is defined with a wide base set of statistics that are relevant and useful to a user and to a user's client. Providing users with this type of report saves them from having to log on to a system and pour through logs from many different sources. This ultimately saves time and money to a system's owner/client, showing explicitly any performance and/or functionality problems with a server and/or network.

In view of the exemplary systems shown and described above, methodologies that may be implemented in accordance with the present invention will be better appreciated with reference to the flow charts of FIGS. 9-13. While, for purposes of simplicity of explanation, the methodologies are shown and described as a series of blocks, it is to be understood and appreciated that the present invention is not limited by the order of the blocks, as some blocks may, in accordance with the present invention, occur in different orders and/or concurrently with other blocks from that shown and described herein. Moreover, not all illustrated blocks may be required to implement the methodologies in accordance with the present invention.

The invention may be described in the general context of computer-executable instructions, such as program modules, executed by one or more components. Generally, program modules include routines, programs, objects, data structures, etc., that perform particular tasks or implement particular abstract data types. Typically the functionality of the program modules may be combined or distributed as desired in various embodiments.

Figure 9:
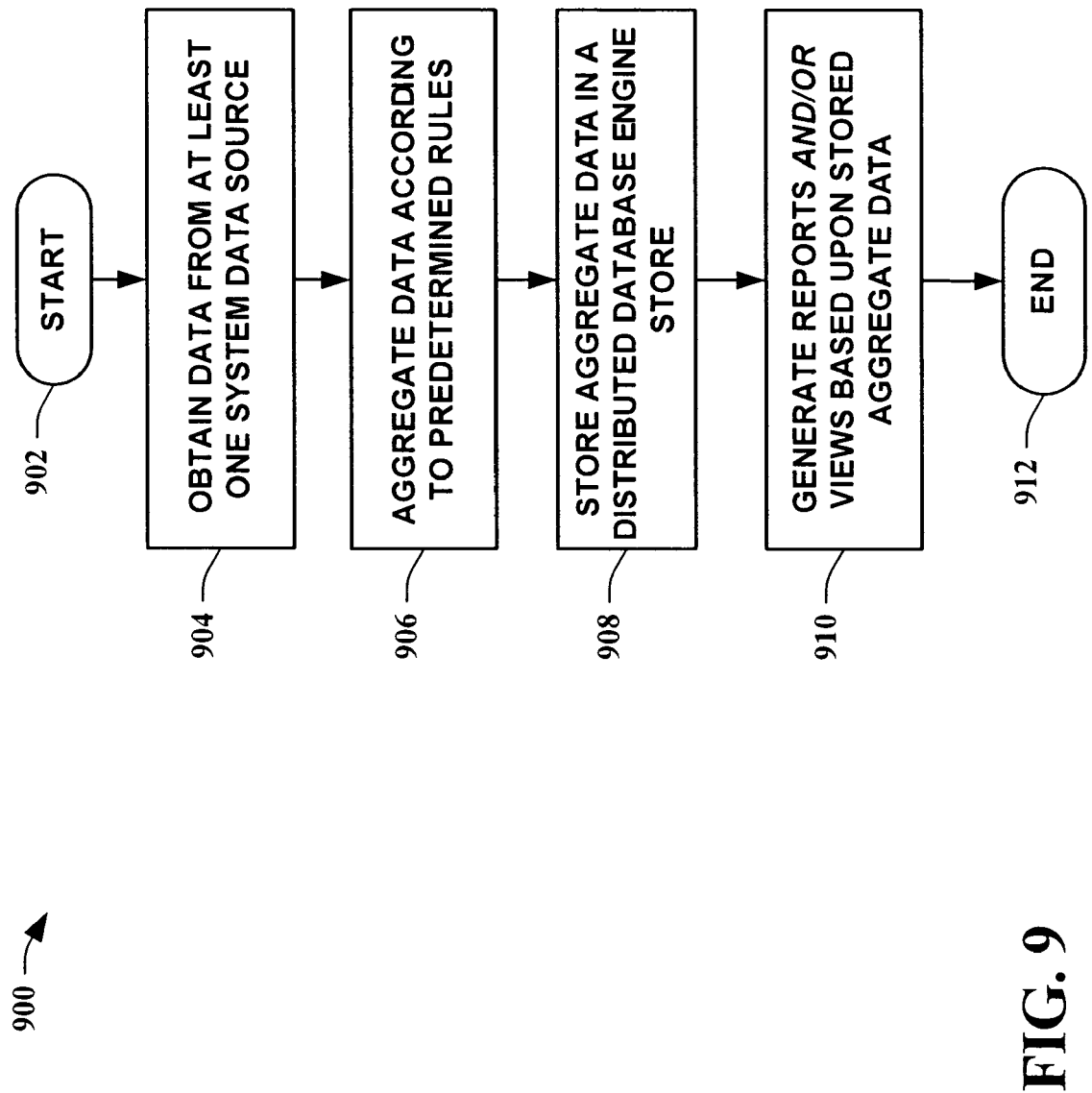
FIG. 9 is a flow diagram of a method of employing aggregated system data in accordance with an aspect of the present invention.

In FIG. 9, a flow diagram of a method 900 of employing aggregated system data in accordance with an aspect of the present invention is shown. The method 900 starts 902 by obtaining data from at least one system data source 904. Data sources can include, but are not limited to, logs, running processes, databases, and other data sources and the like. The data itself can be, but is not limited to, performance data, health data, and utilization data and the like. Any parameter of a system and/or any information that can be utilized in an aggregated form to facilitate an aspect of a system is employable in the present invention. Data can be actively and/or passively obtained. The data is then aggregated according to predetermined rules 906. The predetermined rules can be determined by a user such as a VAP and/or by a system given certain "guidance rules" set by the user and/or by an AI entity that automatically provides rules and/or guidance. These guidance rules allow a system to automatically respond to aggregated data in a desirable fashion. The aggregated data is then stored in a distributed database engine store 908. The distributed database engine store can be a store such as an MSDE store and the like. Reports and/or views based upon the stored aggregate data are then generated 910, ending the flow 912. The generated information is typically based upon a desired user request that is stimulated by a predetermined request and/or determined by a customized user request set. The generated information can include, but is not limited to, aggregated information and/or aggregated data mined information such as trend data and/or prediction data. The present invention also provides a means for regressing a system's state when changes have been made to the system that cause unexpected results. A user can initiate a "return to previous state X" to provide for a functioning system once again. This can be accomplished by a system utilizing prior aggregated data to determine the previous state X. In the same fashion, remedial action can be taken when aggregated data indicates problems that a system can automatically respond to such as, for example, when a disk low error is detected, temporary files could be automatically deleted to gain more disk space, avoiding a disk crash. Likewise, security holes and hacking attempts can be avoided by utilizing the aggregated data and automatically downloading a security fix and/or shutting down a vulnerable server and the like.

Figure 10:
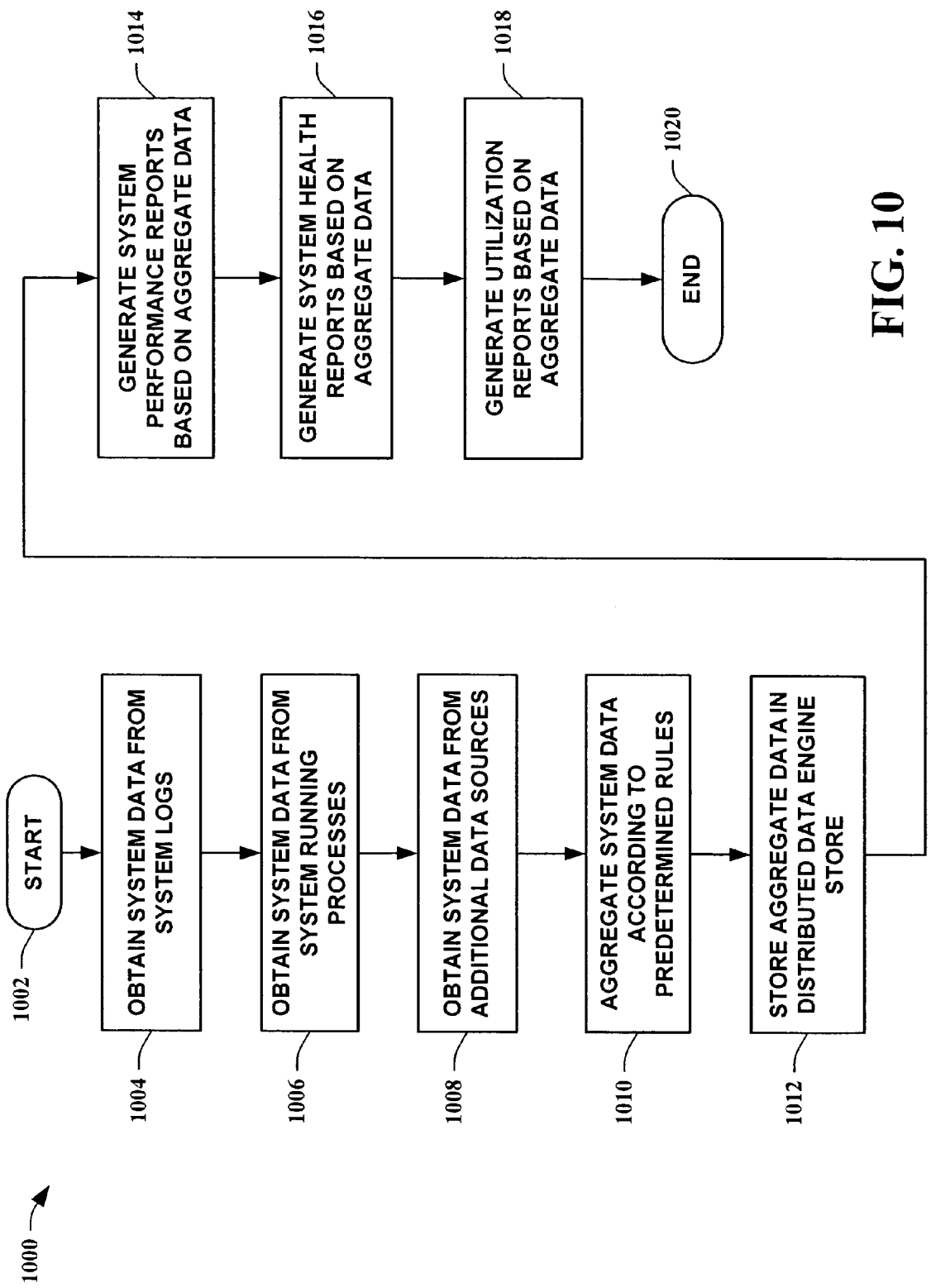
FIG. 10 is another flow diagram of a method of employing aggregated system data in accordance with an aspect of the present invention.

Referring to FIG. 10, another flow diagram of a method 1000 of employing aggregated system data in accordance with an aspect of the present invention is depicted. The method 1000 starts 1002 by obtaining system data from system logs 1004. The logs can include, but are not limited to, exchange logs, fax logs, VPN logs, IIS logs, event logs, and RRAS internet connection logs and the like. System data is also obtained from processes running in the system 1006. These processes can include, but are not limited to, health monitoring processes, performance monitoring processes, and utilization monitoring processes and the like. Additional system data is also obtained from other system data sources 1008. These additional data sources can include, but are not limited to, health monitor databases, performance monitoring databases, and utilization monitoring databases and the like. Data can be obtained in a variety of means such as, for example, by direct polling and/or transmission by data sources themselves such as via broadcasts, multicasts, and/or unicasts and the like. The system data is then aggregated according to predetermined rules 1010. The predetermined rules can be determined by a user such as a VAP and/or by a system given certain "guidance rules" set by the user and/or by an AI entity. These guidance rules allow a system to automatically respond to aggregated data in a desirable fashion. The aggregate data is then stored in a distributed data engine store 1012. This permits easy distribution of the data to a user. Initiated by a user and/or automatically by a system, performance related reports and/or views are generated based on the aggregated performance data stored in the distributed data engine store 1014. Likewise, health related reports are generated based on the aggregated health data stored in the distributed data engine store 1016. The generated health reports/views are initiated like the performance reports/views either by a user and/or automatically by a system. Utilization reports and/or views are also generated based on the utilization aggregated data found on the distributed data engine store 1018, ending the flow 1020. Again, the reports/view can be initiated by a user and/or automatically by a system. Thus, the present invention provides flexibility of not only employing different types of data, but also in aggregation rules, and in generating information to be utilized either by a system for automatic control/artificial intelligence, or by a user responding to the generated information.

Figure 11:
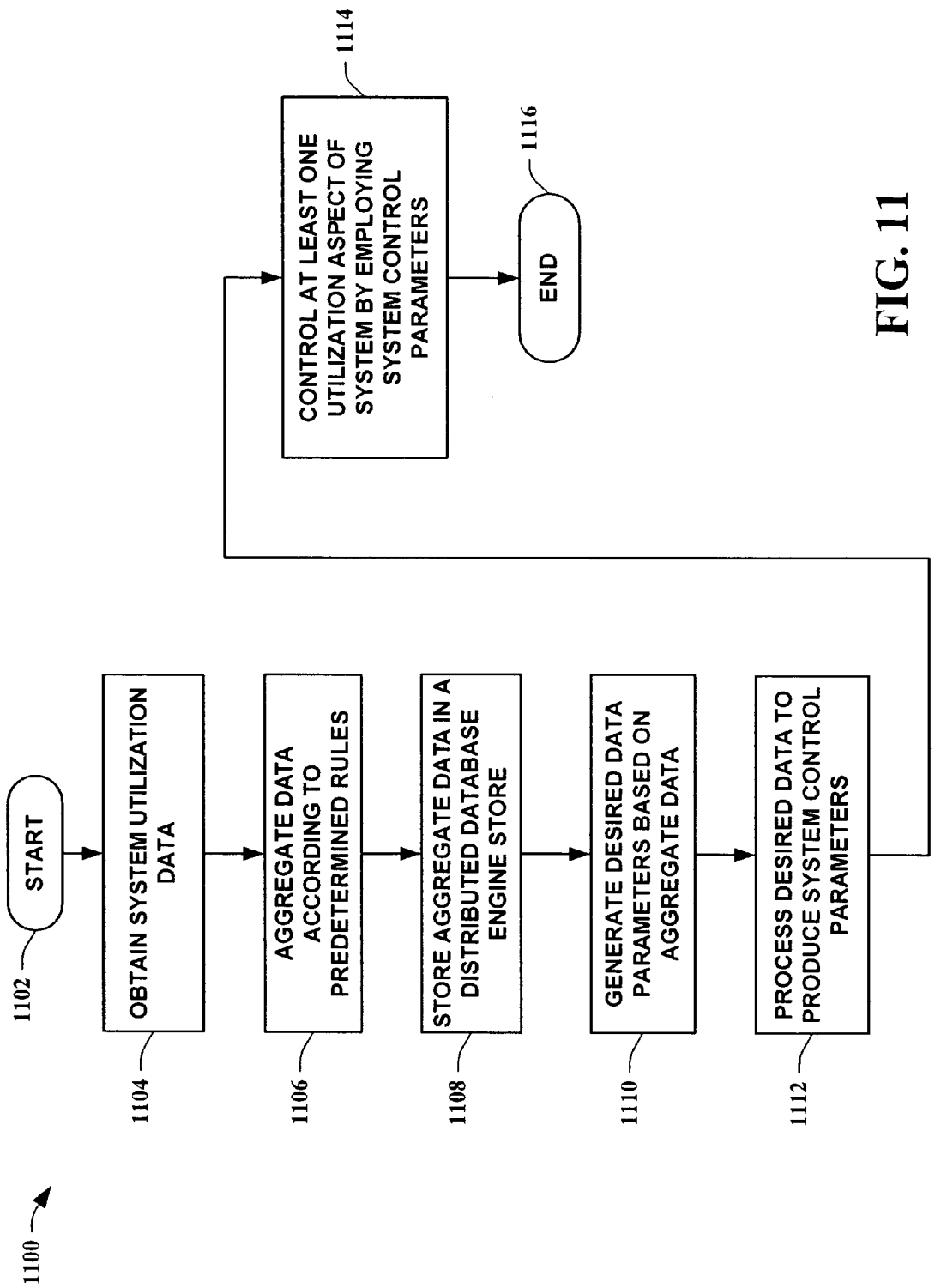
FIG. 11 is a flow diagram of a method of controlling system utilization in accordance with an aspect of the present invention.

Turning to FIG. 11, a flow diagram of a method 1100 of controlling system utilization in accordance with an aspect of the present invention is illustrated. The method 1100 starts 1102 by obtaining system utilization data from a system 1104. The utilization data is aggregated according to predetermined rules 1106. The predetermined rules can be determined by a user such as a VAP and/or by a system given certain "guidance rules" set by the user and/or an AI entity. These guidance rules allow a system to automatically respond to aggregated data in a desirable fashion. The present invention can also utilize artificial intelligence to take the place of the guidance rules set by the user. This allows a system to be completely autonomous. The aggregated utilization data is then stored in a distributed database engine store 1108. This permits access to the data by a user and/or by a system. Desired data parameters are then generated based on the aggregated utilization data stored on the distributed database engine store 1110. Desired parameters can include, but are not limited to, internet bandwidth of single system user, internet bandwidth of an entire system, memory utilization of a system, storage utilization of a server, e-mail utilization of a single system user and/or a group of system users, and any data that can indicate utilization of a system as a whole and/or of an individual system user and/or group of system users and the like. The desired data parameters can be derived from necessary data required for a particular control command and the like so that a system can automatically respond to the parameter and/or enable a capability to allow a manual response. Thus, the desired data is processed to produce system control parameters 1112. The system control parameters can be indicated actions to a user either by reporting a certain level of activity needing investigation and/or a response suggestion that can be easily initiated by a predetermined response pattern/sequence. The system control parameters can also be formulated to provide direct responses to an automated system for controlling a system's utilization. This allows control of at least one utilization aspect of a system by employing the system control parameters 1114, ending the flow 1116. The controlled aspect, whether automatic and/or via a user input, can include such things as limiting bandwidth, limiting emails, limiting faxes, limiting internet usage, and/or limiting other system assets. The system control parameters can also be utilized to load shed during high peak periods and the like at critical utilization maximums and/or utilized to load balance between more than one system and/or between more than one server in one or more systems. The control parameters can also be employed in management and/or productivity tools relating to end-users of a system. In this manner productivity can be increased through periodic and/or aperiodic interfacing with system utilization related data. Utilization data can also be employed to prioritize utilization of a system. For example, if boss X wants to process payroll, the initiation of the payroll process causes junior employee's internet downloading processes to be subservient to the boss X's payroll process automatically.

Figure 12:
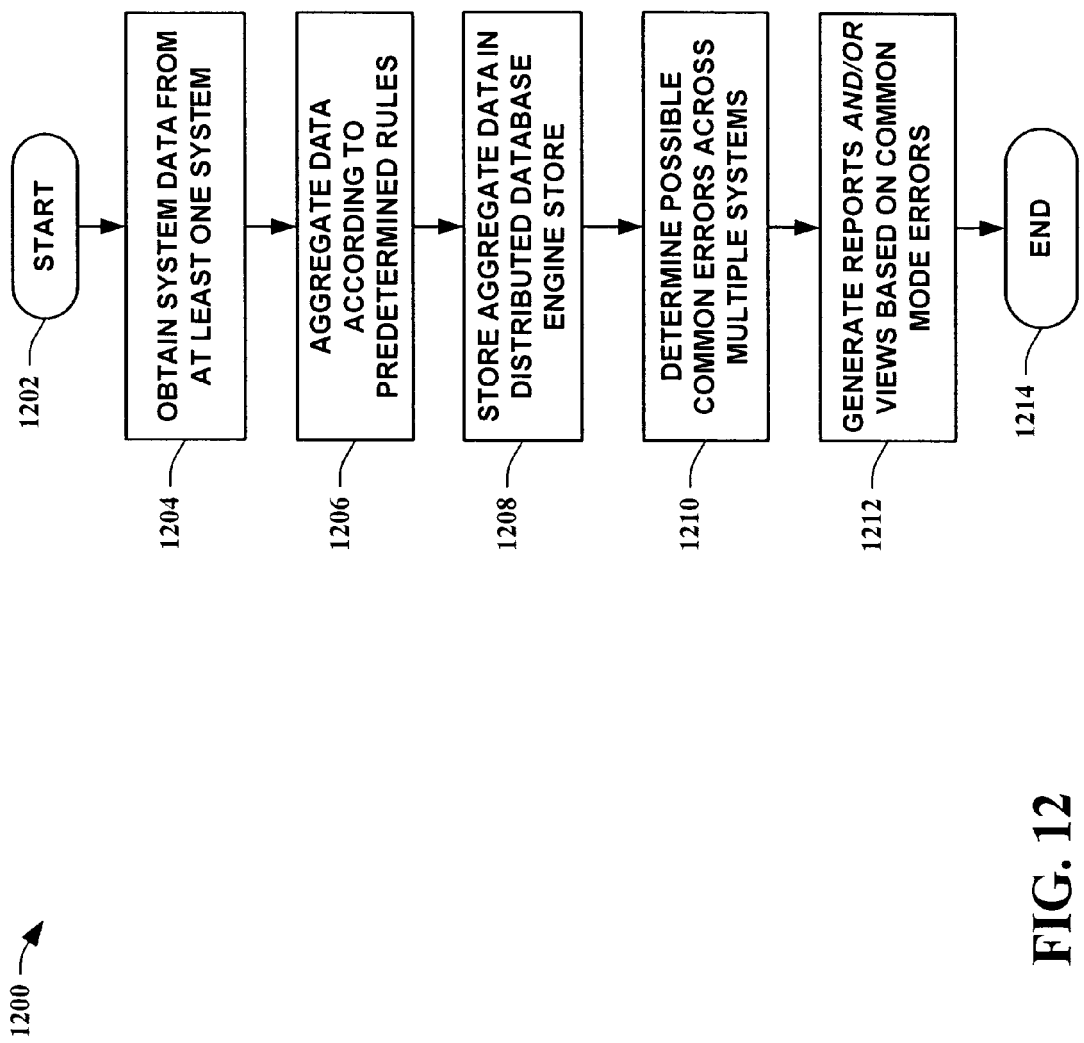
FIG. 12 is a flow diagram of a method of detecting common errors in accordance with an aspect of the present invention.

Looking at FIG. 12, a flow diagram of a method 1200 of detecting common errors in accordance with an aspect of the present invention is shown. The method 1200 starts 1202 by obtaining system data from at least one system 1204. The system data is aggregated according to predetermined rules 1206. The predetermined rules can be determined by a user such as a VAP and/or by a system given certain "guidance rules" set by the user and/or an AI entity. These guidance rules allow a system to automatically respond to aggregated data in a desirable fashion. The aggregated data is then stored in a distributed database engine store for easy access 1208. A determination is then made as to whether the aggregated data indicates possible common errors that occur across multiple servers and/or multiple systems 1210. Common errors can be associated with common hardware and/or common software. Thus, part of the aggregated data typically contains configuration data for servers and/or systems. It is not uncommon for a particular piece of hardware to have a "common mode failure" that can appear in other devices utilizing that particular piece of hardware and/or can appear when a given particular software thread is run. By utilizing this information in an aggregate form, common errors can be eliminated by intervention and/or masking if they create false alerts. Thus, reports and/or views based on the common mode errors are generated 1212, ending the flow 1214. System control commands can also be generated to allow an automatic response by a system to a possibly harmful and/or catastrophic type hardware and/or software failure. Similarly, the present invention can be utilized to automatically fix simpler problems if it is aware of a correct system state for a given system. For example, if a single process takes 100% of a system's CPU processing time for more than a given amount of time, for example—10 minutes, and the process has not been indicated as a critical operation, the process can be throttled to ensure that the rest of the system remains responsive. A report can then be generated notifying a system administrator and/or a system owner that a problem exists and that it has been mitigated to avoid any apparent adverse effects to a system's users. The present invention also provides a means to notify and/or automatically update software and the like when potential problems and/or software bugs appear. In this manner, software fixes can be automatically loaded without a VAP's intervention. Likewise, if an immediate fix is not available for a known bug in a software version, the error can be masked so as to not appear as a false alert to a system and/or a user. The aggregated data can also show trends and/or patterns that might indicate a possible disastrous situation and/or possibly an intentional attack on a server and/or system.

Figure 13:
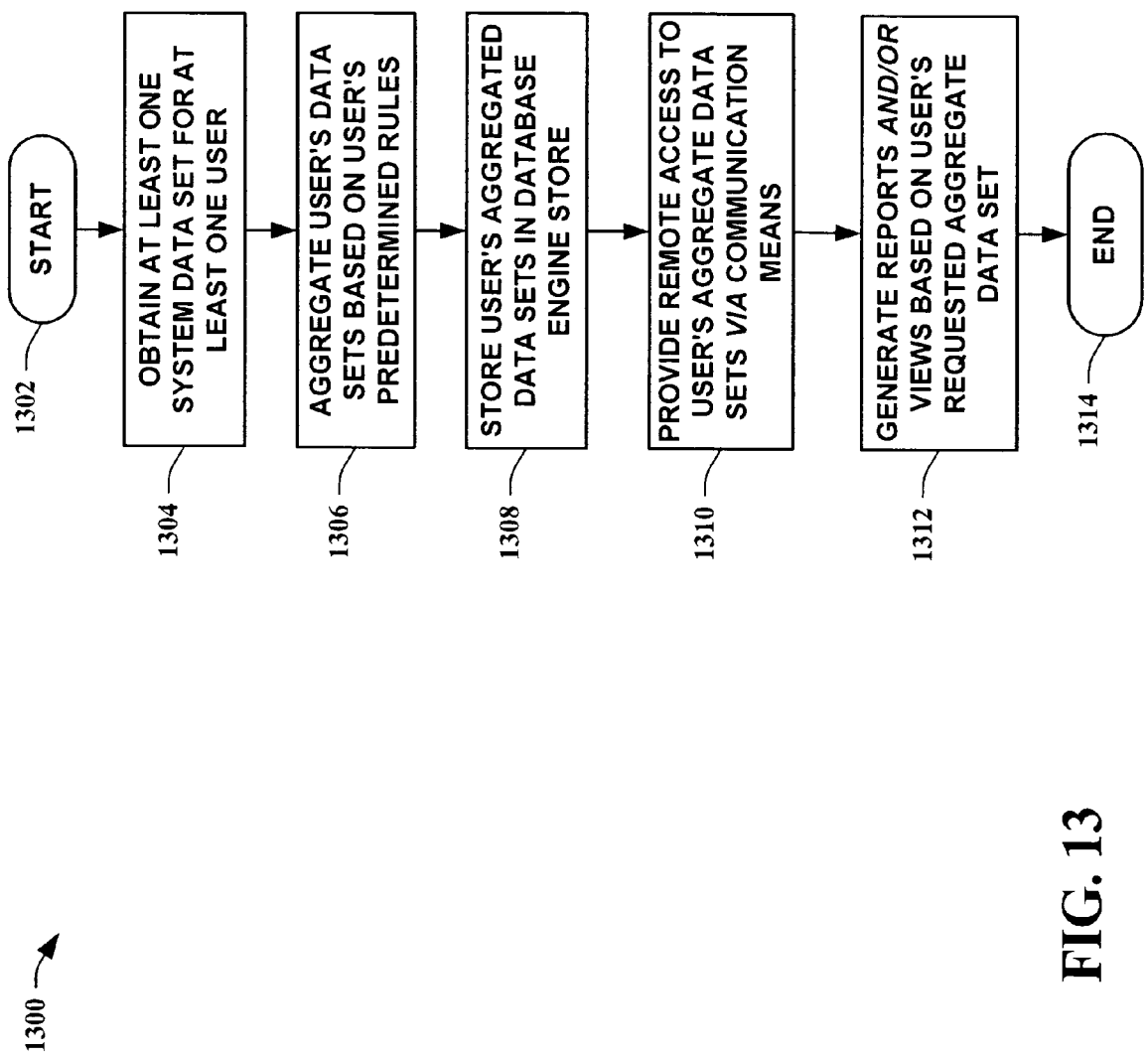
FIG. 13 is a flow diagram of a method of servicing multiple systems in accordance with an aspect of the present invention.

Referring to FIG. 13, a flow diagram of a method 1300 of servicing multiple systems in accordance with an aspect of the present invention is depicted. The method 1300 starts 1302 by obtaining at least one system data set for at least one user (e.g., VAP) 1304. System data sets that belong to a particular user (VAP) are aggregated according to that user's predetermine rules 1306. Likewise, each additional set, if applicable, of system data is also aggregated according to each individual user. This permits, for example, a single computing and/or hosting entity to provide system aggregation and/or control services for multiple users (VAPs) in a single and/or "apparently" single remote location to the users. The aggregated data sets are then stored in a database engine store for easy retrieval 1308. Remote access is then provided to any number of users for accessing their aggregate data via a communication means 1310. The communication means can include, for example, the Internet, telecommunications, radio communications, and satellite communications and the like. Reports and/or views based on a particular user's aggregated system data is generated in response to a user query and/or a user's system 1312, ending the flow 1314. Thus, the present invention provides a means to allow the output to directly control the user's system and/or prompt a user of alerts via paging, emails, and telephone calls and the like without requiring the user to be at any particular terminal to access information regarding systems under their administration.

Figure 14:
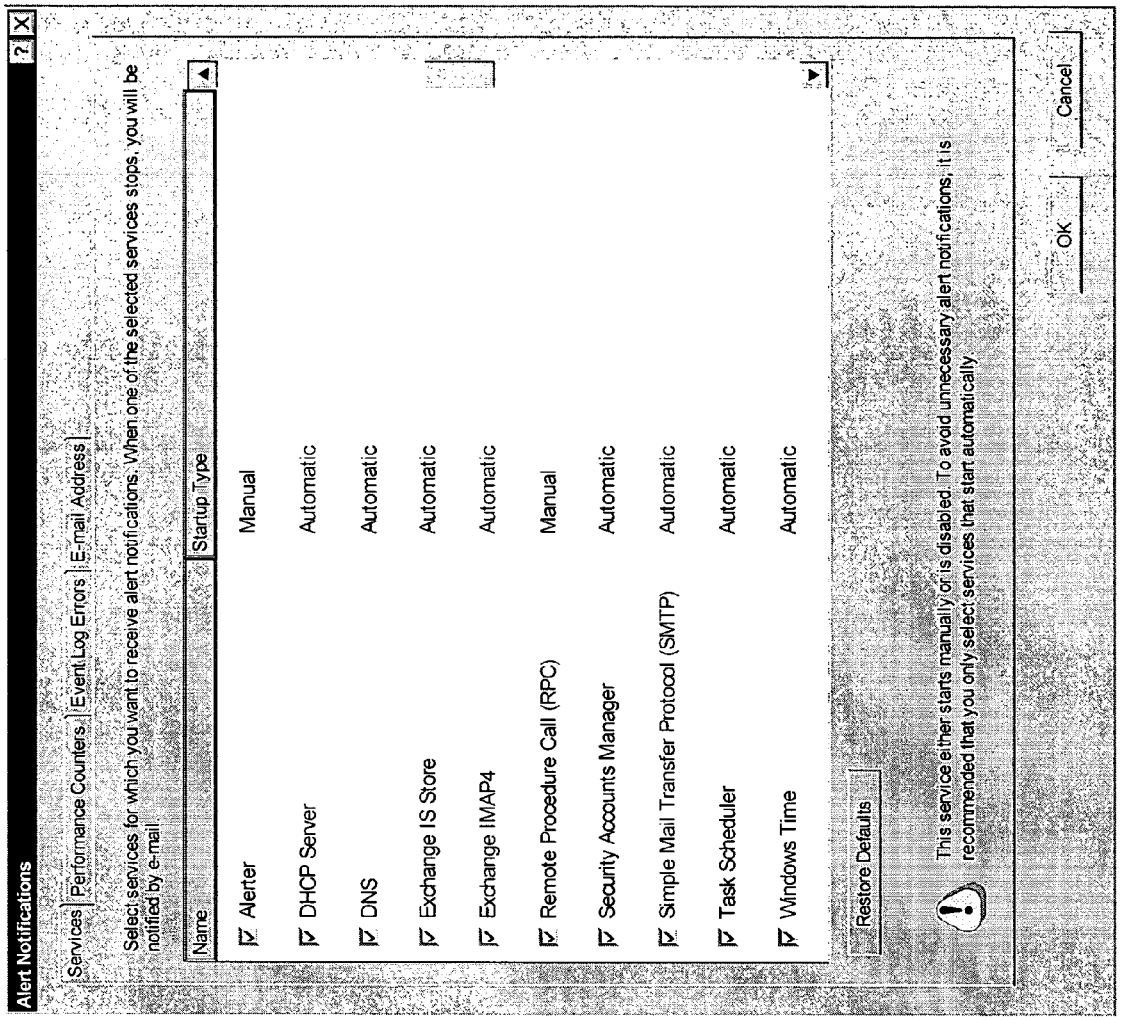
FIG. 14 is a screen shot of an alert notification user interface in accordance with an aspect of the present invention.
Figure 15:
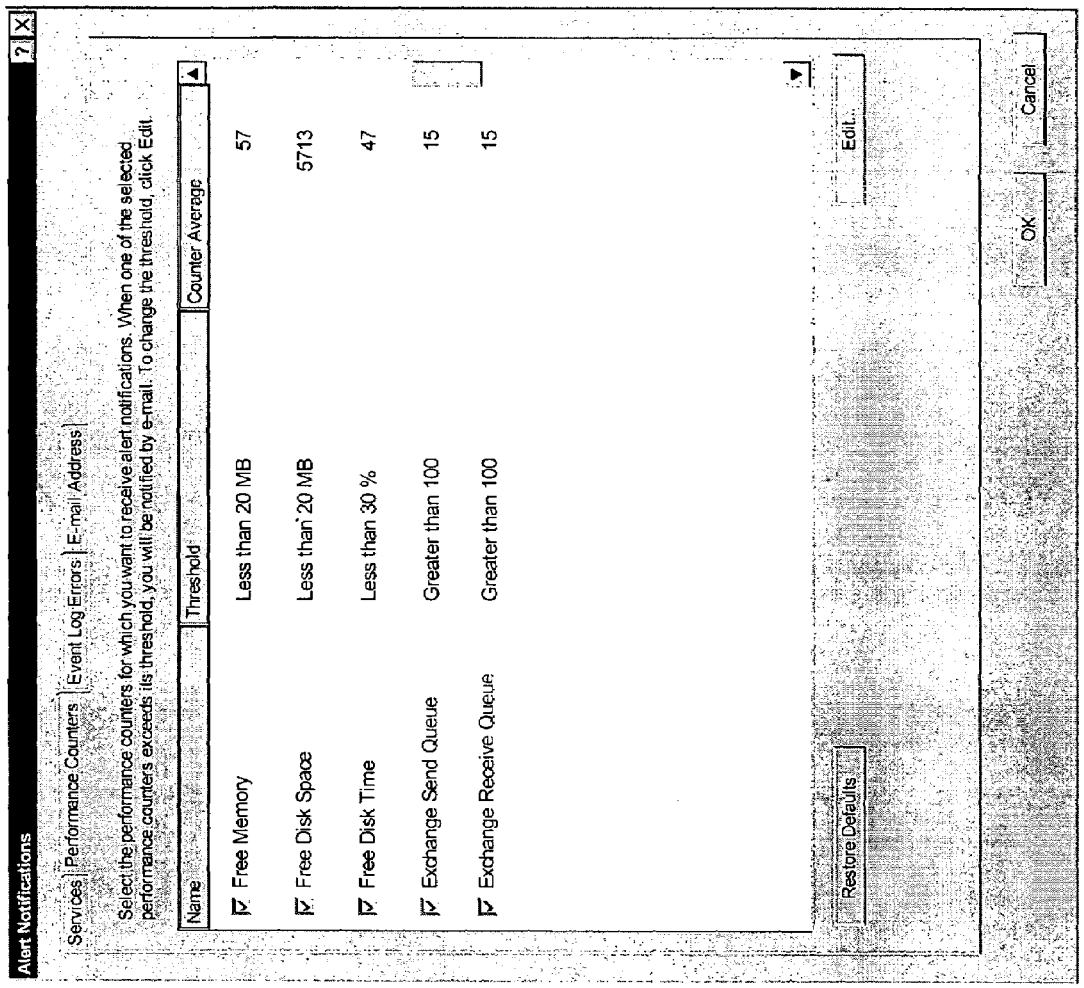
FIG. 15 is another screen shot of an alert notification user interface in accordance with an aspect of the present invention.
Figure 16:
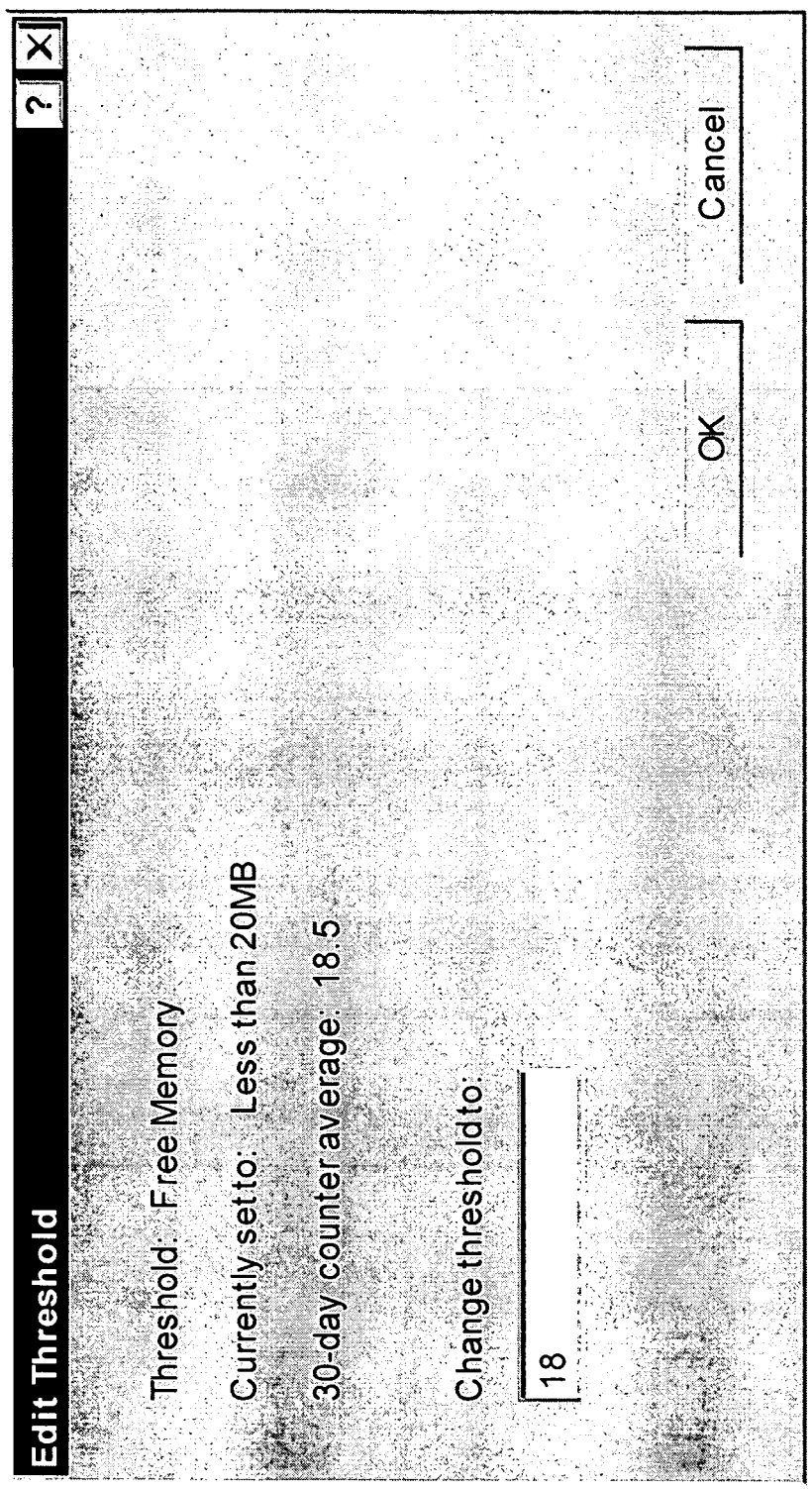
FIG. 16 is a screen shot of an alert threshold edit user interface in accordance with an aspect of the present invention.

The present invention additionally employs the supra structures and methods to provide graphical user interfaces to facilitate information dissemination to a user such as, for example, a system administrator and/or a system owner such as, for example, a system administrator's client. Different UI configurations can be created utilizing the present invention. In one instance of the present invention, a health monitor configuration UI is provided. This UI permits a user to configure appropriate alerts and settings relating to a server and/or a system that the user administers. In this manner the user can modify and set such aspects of a health monitor function such as alert thresholds, notification means for alerts, and which alerts to monitor for a server and/or a network and the like. An example UI for setting alert notifications is illustrated in an alert notifications UI 1400 shown in FIG. 14. The present invention provides access to historical data allowing averages of past data to be calculated to facilitate a user in choosing appropriate alert thresholds, shown in another view of the alert notifications UI 1500 in FIG. 15. Thus, an average of the last 30 days, for example, can be displayed for a monitored alert. The alert notifications UI 1500 also illustrates that individual alert notifications can be enabled or disabled. An alert threshold edit UI 1600 is shown in FIG. 16. This UI 1600 provides a means to individually edit and/or set a threshold for an alert. In this illustration 1600, the alert is currently set to "less than 20 MB" and a 30-day average for the system and/or server of 18.5 MB. Thus, a user easily recognizes that the free memory has fallen below the 20 MB threshold during the last 30 day period. If utilizing 18.5 MB is still acceptable to the user, they can change the alert threshold to 18 MB as illustrated in this example to avoid receiving any further unnecessary alerts.

Figure 17:
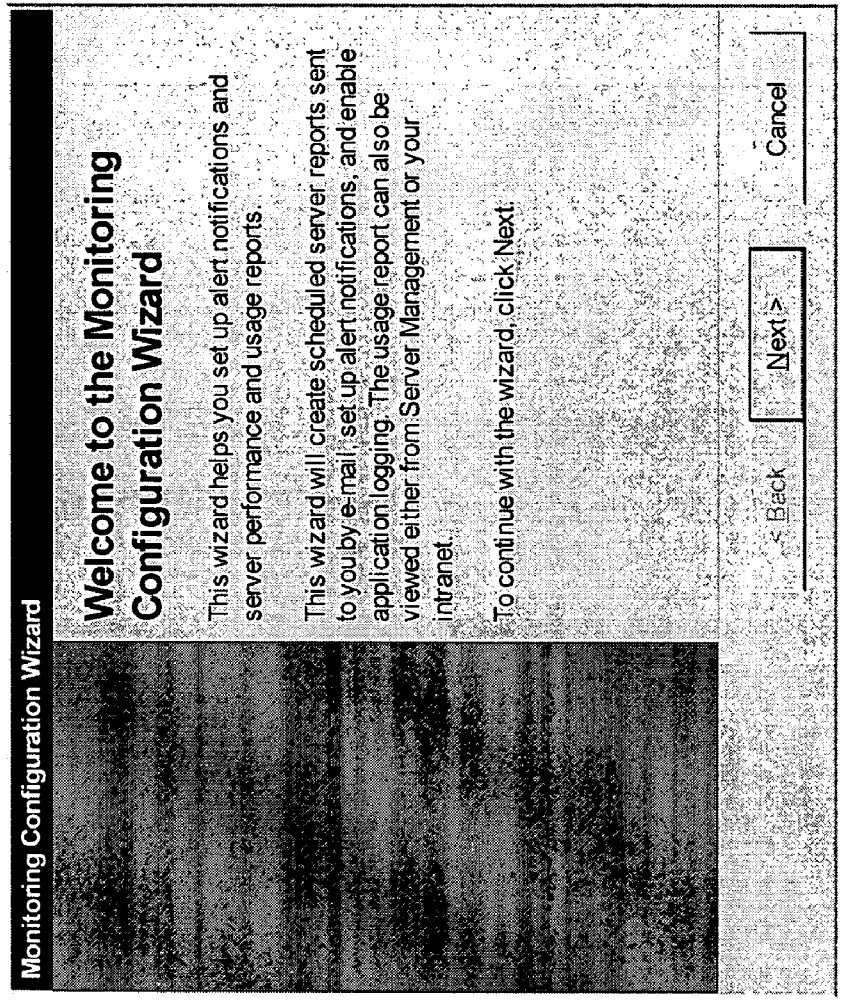
FIG. 17 is a screen shot of a monitoring configuration user interface in accordance with an aspect of the present invention.
Figure 18:
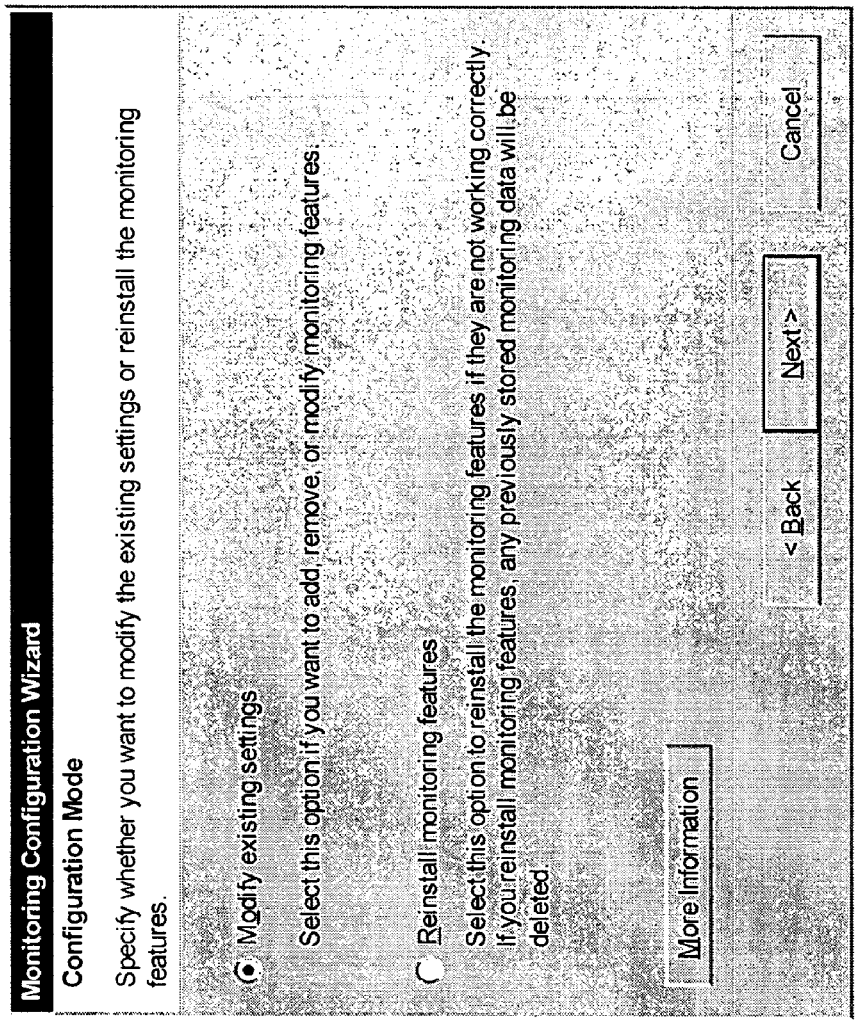
FIG. 18 is a screen shot of a mode selection user interface in accordance with an aspect of the present invention.
Figure 19:
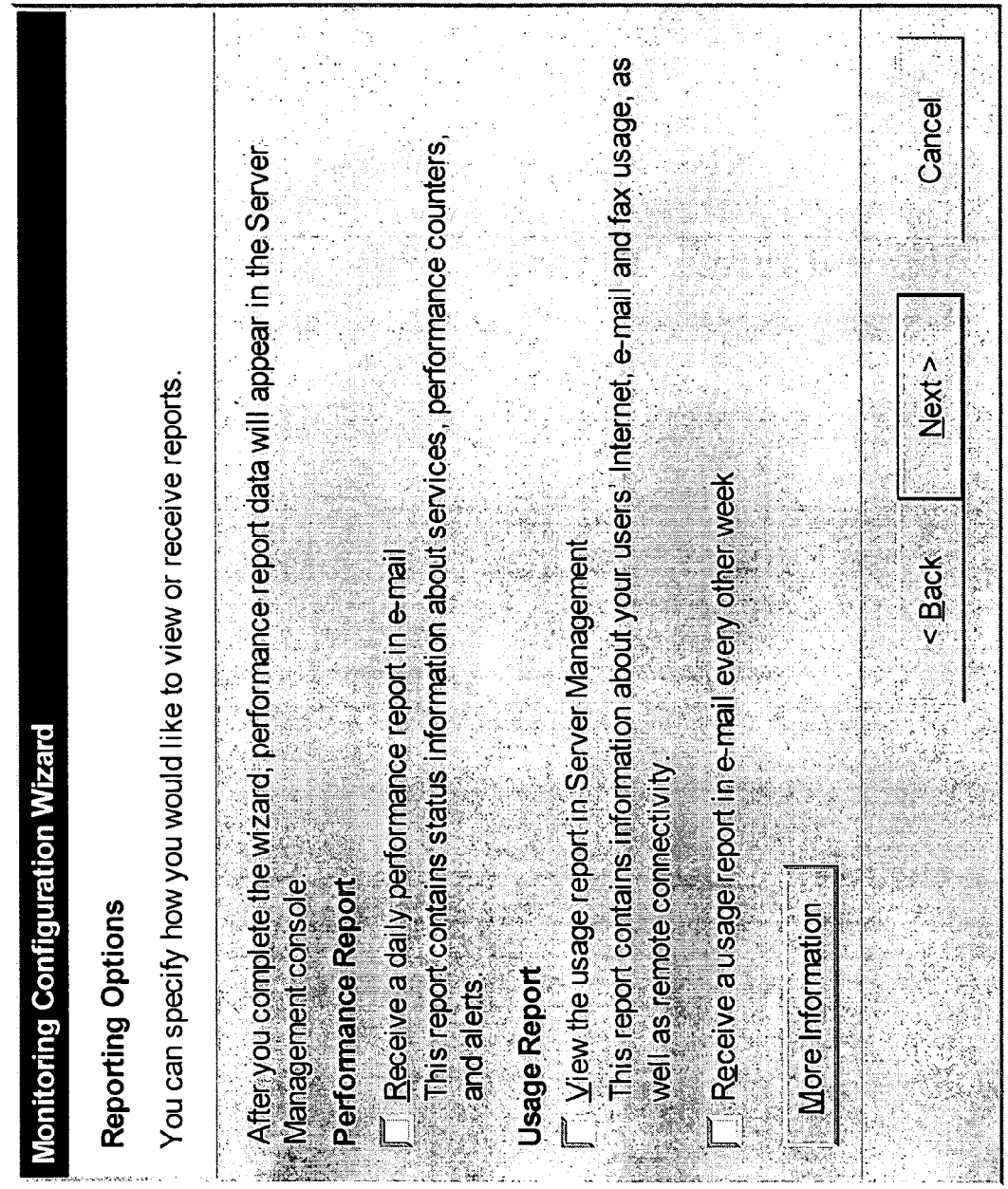
FIG. 19 is a screen shot of a reporting options user interface in accordance with an aspect of the present invention.
Figure 20:
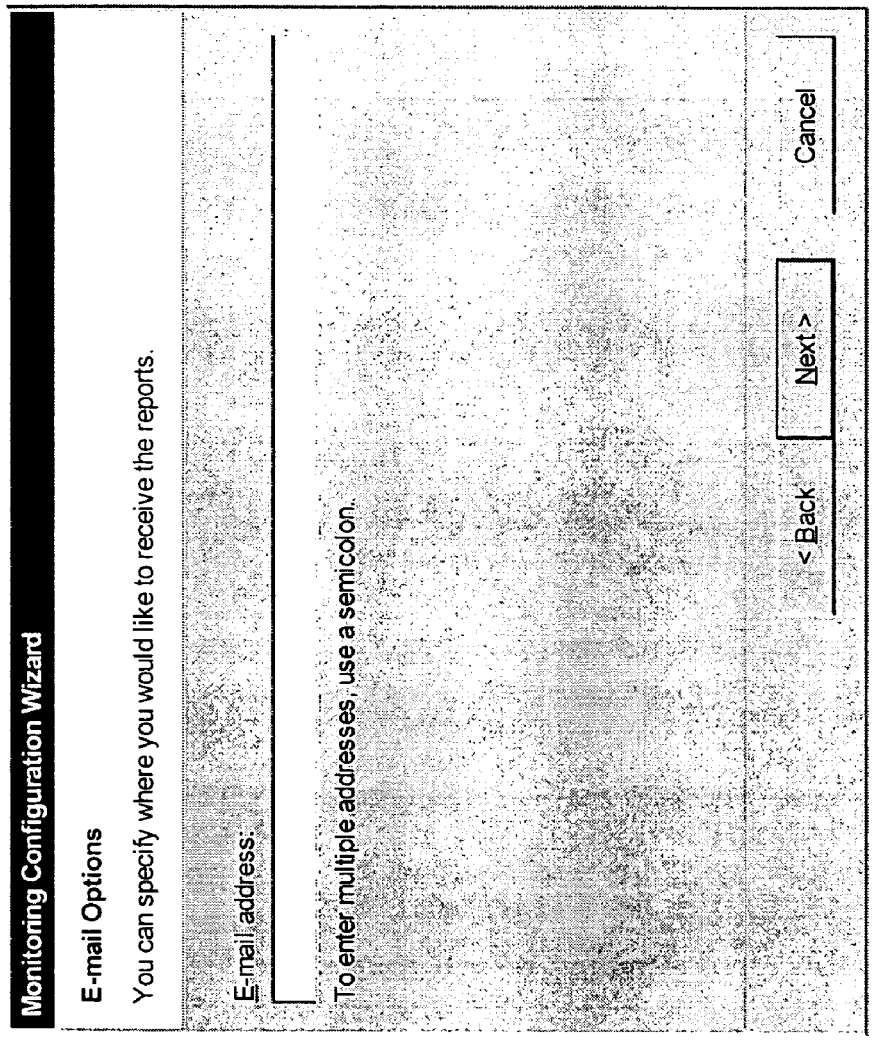
FIG. 20 is a screen shot of an e-mail options user interface in accordance with an aspect of the present invention.
Figure 21:
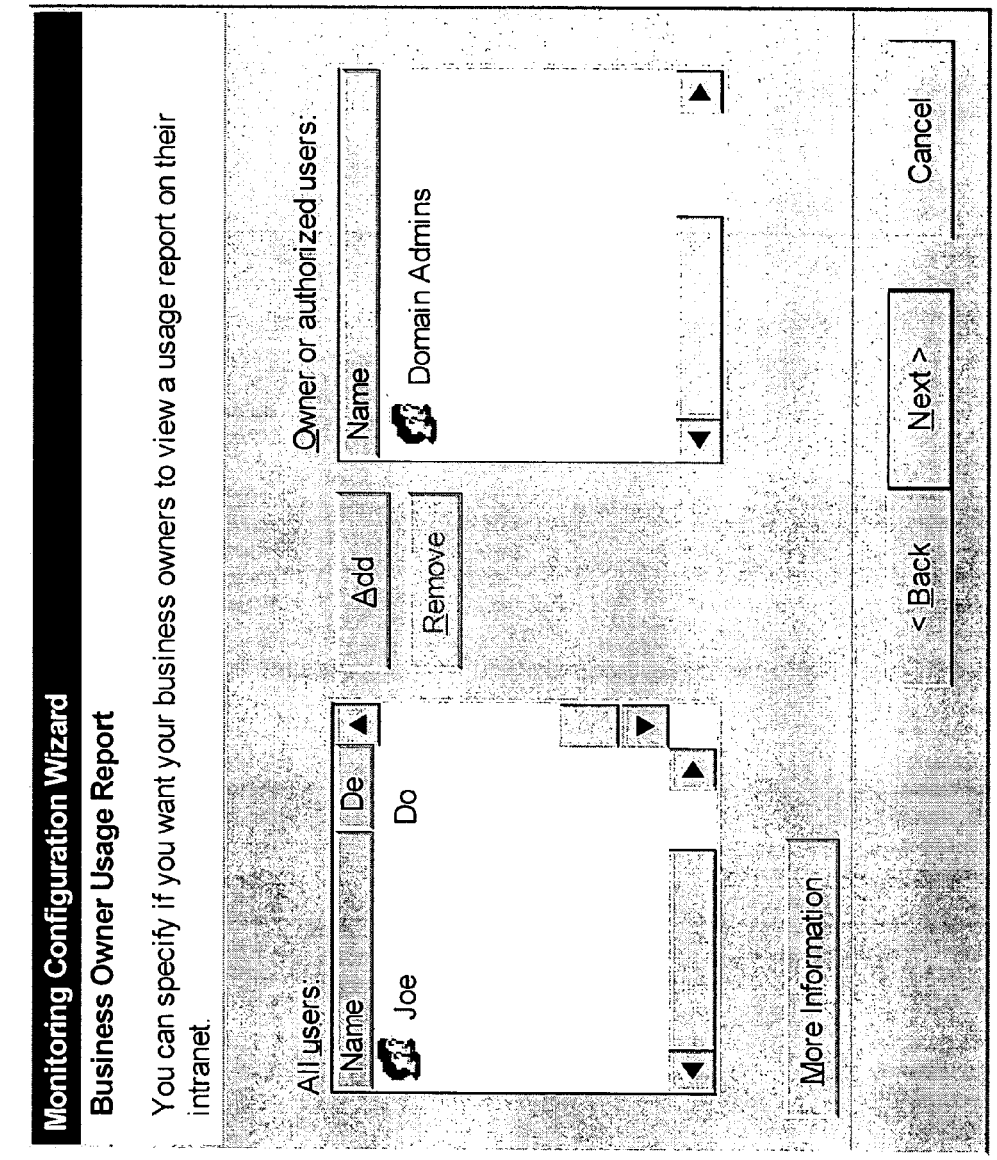
FIG. 21 is a screen shot of a business owner usage report user interface in accordance with an aspect of the present invention.
Figure 22:
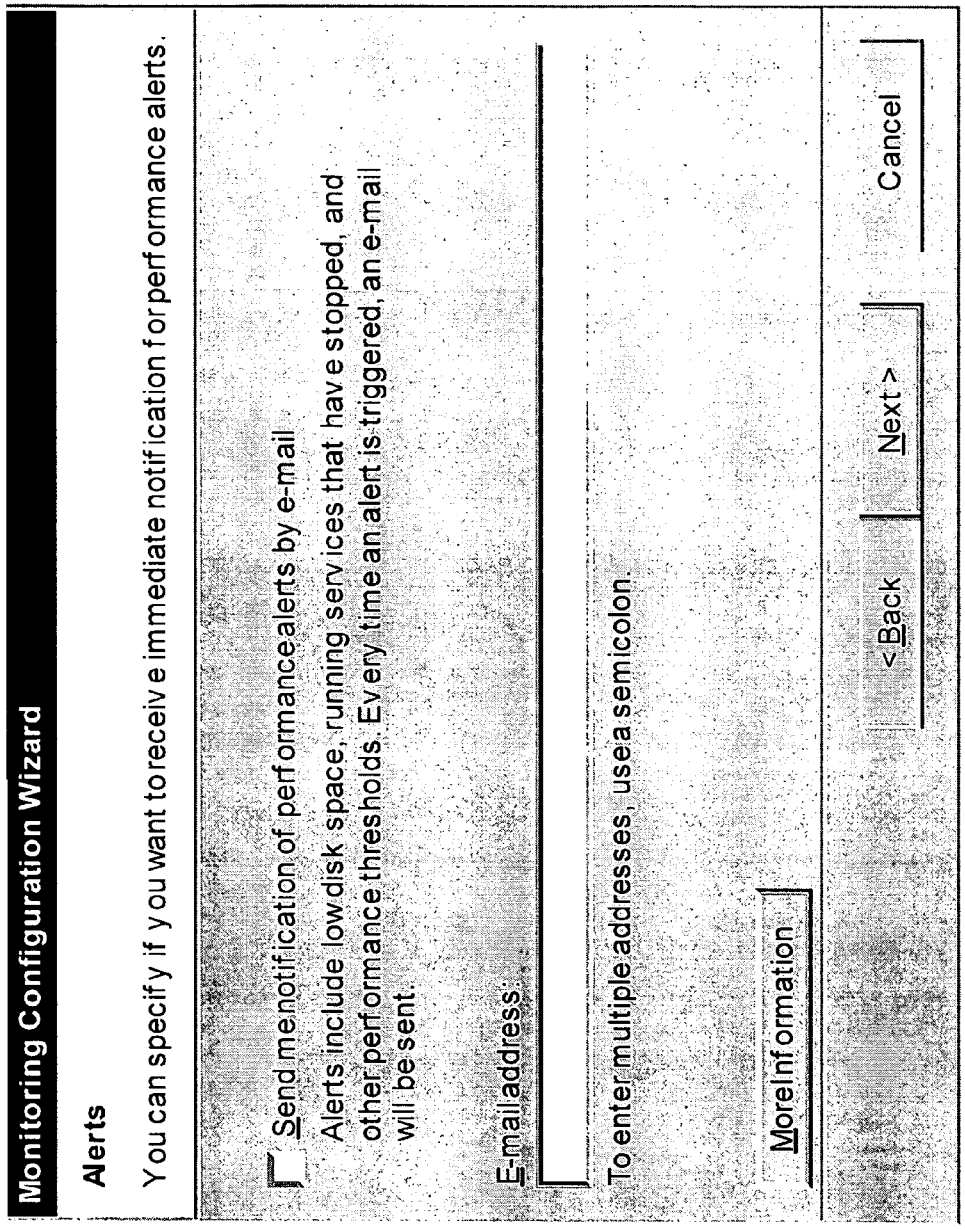
FIG. 22 is a screen shot of an alerts user interface in accordance with an aspect of the present invention.
Figure 23:
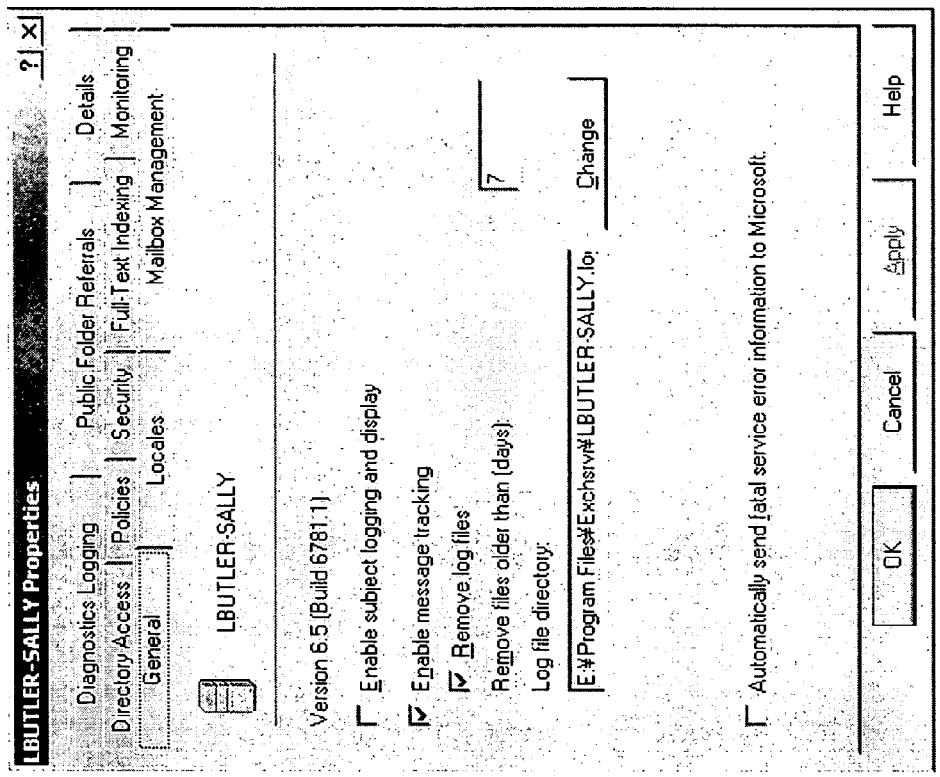
FIG. 23 is a screen shot of a user's property settings user interface in accordance with an aspect of the present invention.
Figure 24:
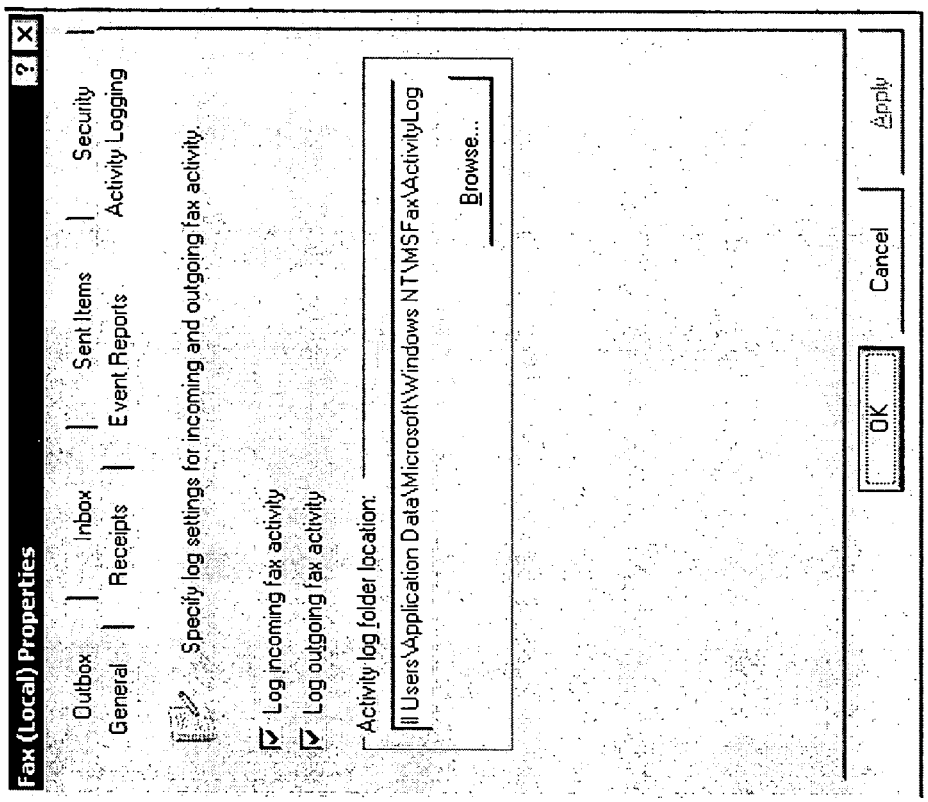
FIG. 24 is a screen shot of a fax property settings user interface in accordance with an aspect of the present invention.
Figure 25:
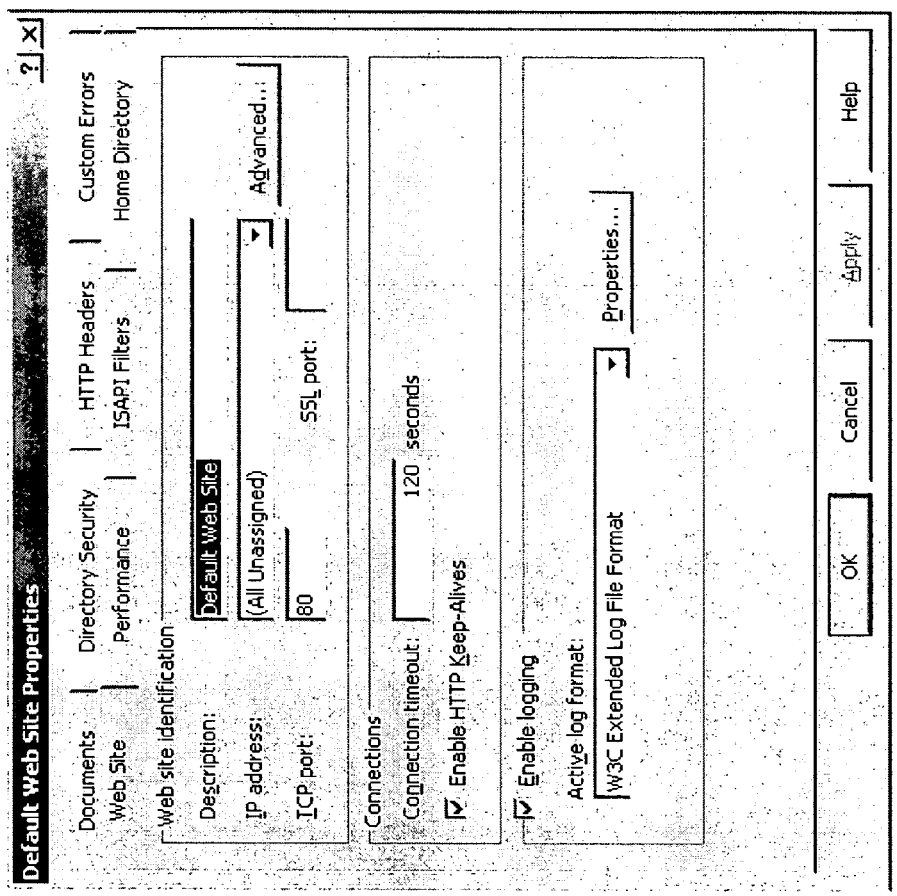
FIG. 25 is a screen shot of a default web site property settings user interface in accordance with an aspect of the present invention.
Figure 26:
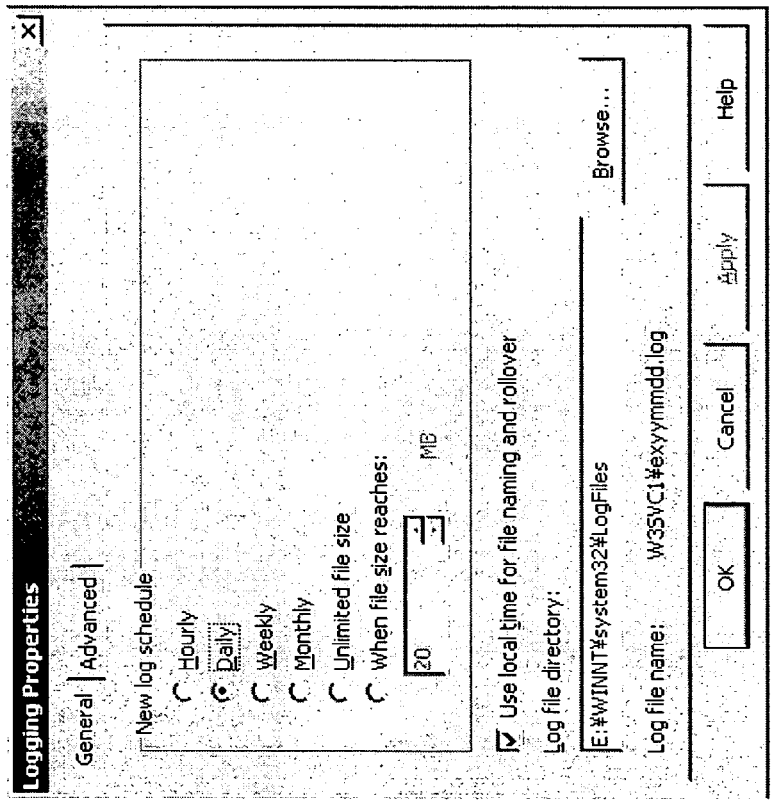
FIG. 26 is a screen shot of a logging property settings user interface in accordance with an aspect of the present invention.
Figure 27:
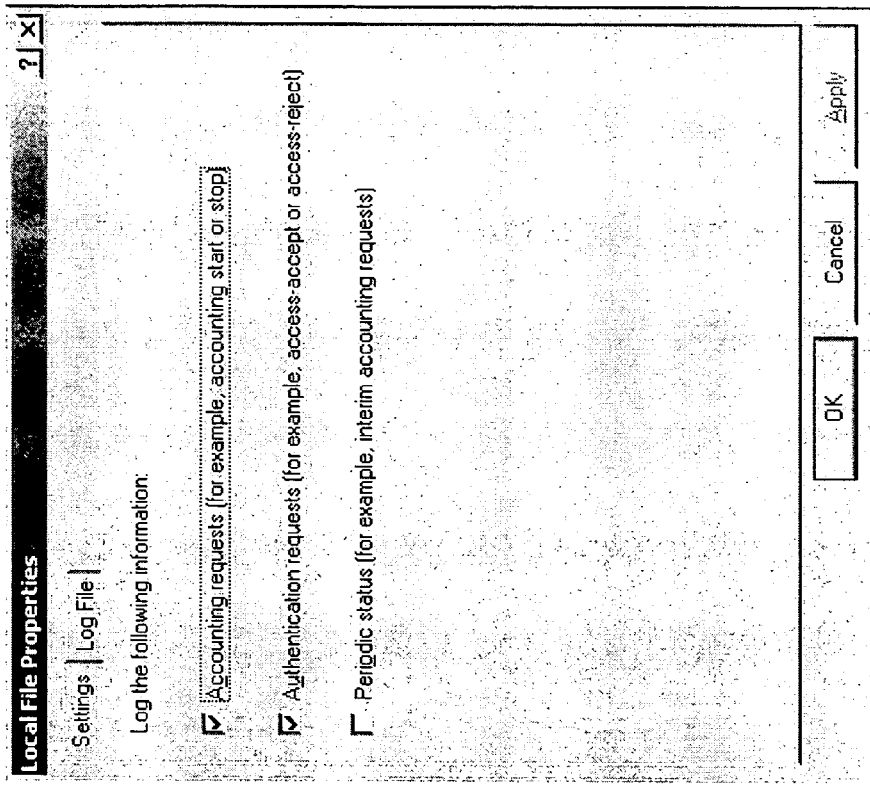
FIG. 27 is a screen shot of a local file property settings user interface in accordance with an aspect of the present invention.
Figure 28:
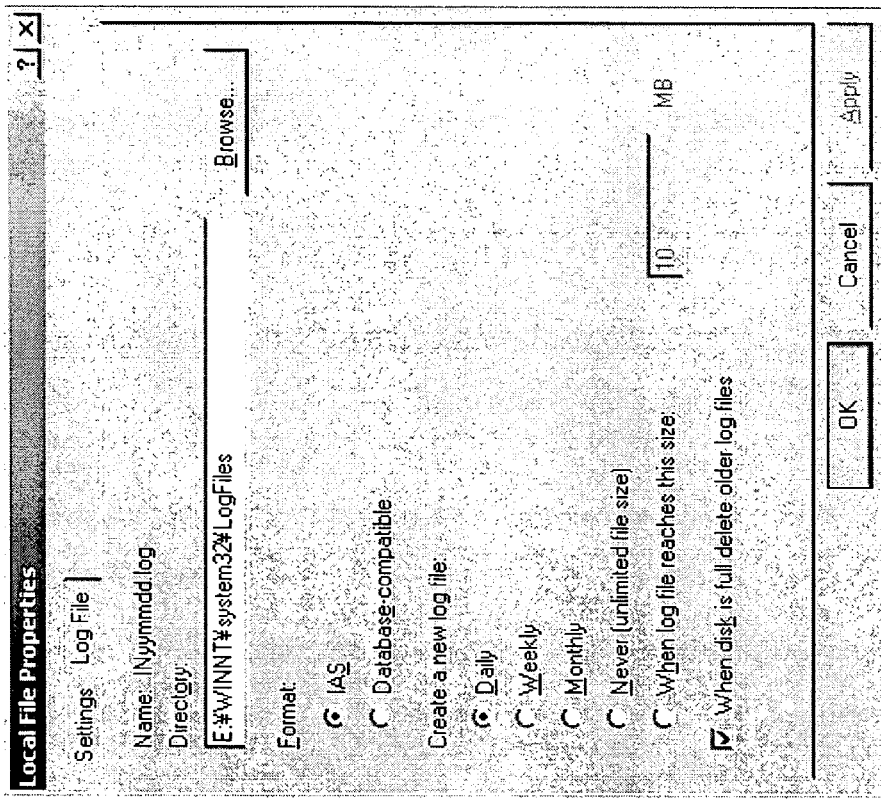
FIG. 28 is a screen shot of a local file property log file settings user interface in accordance with an aspect of the present invention.
Figure 29:
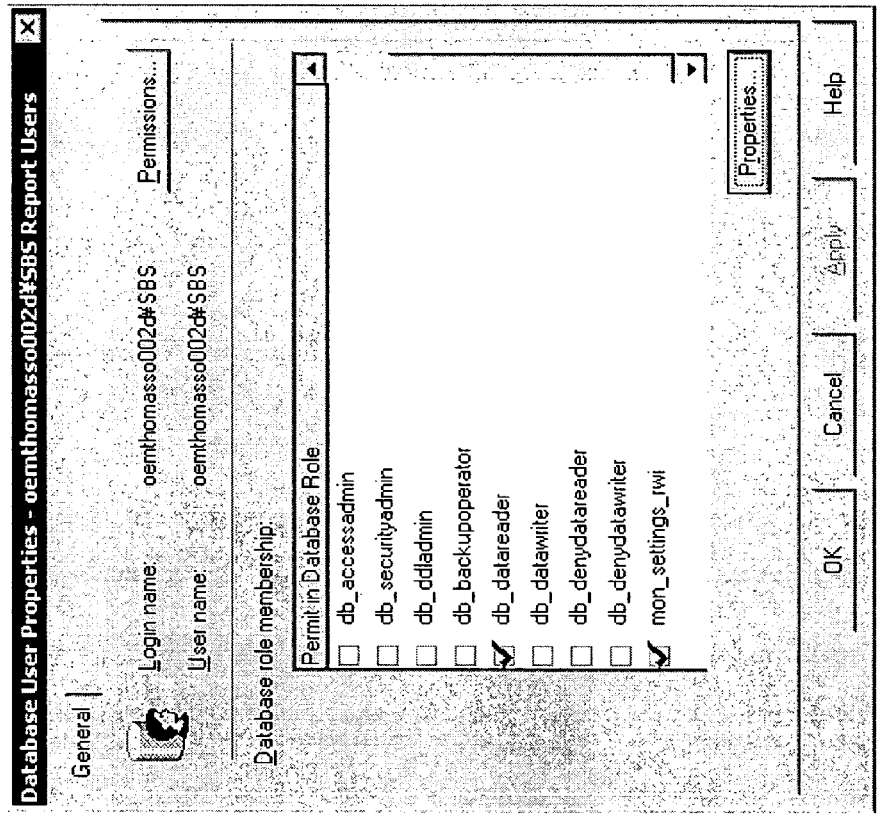
FIG. 29 is a screen shot of a database user property settings user interface in accordance with an aspect of the present invention.
Figure 30:
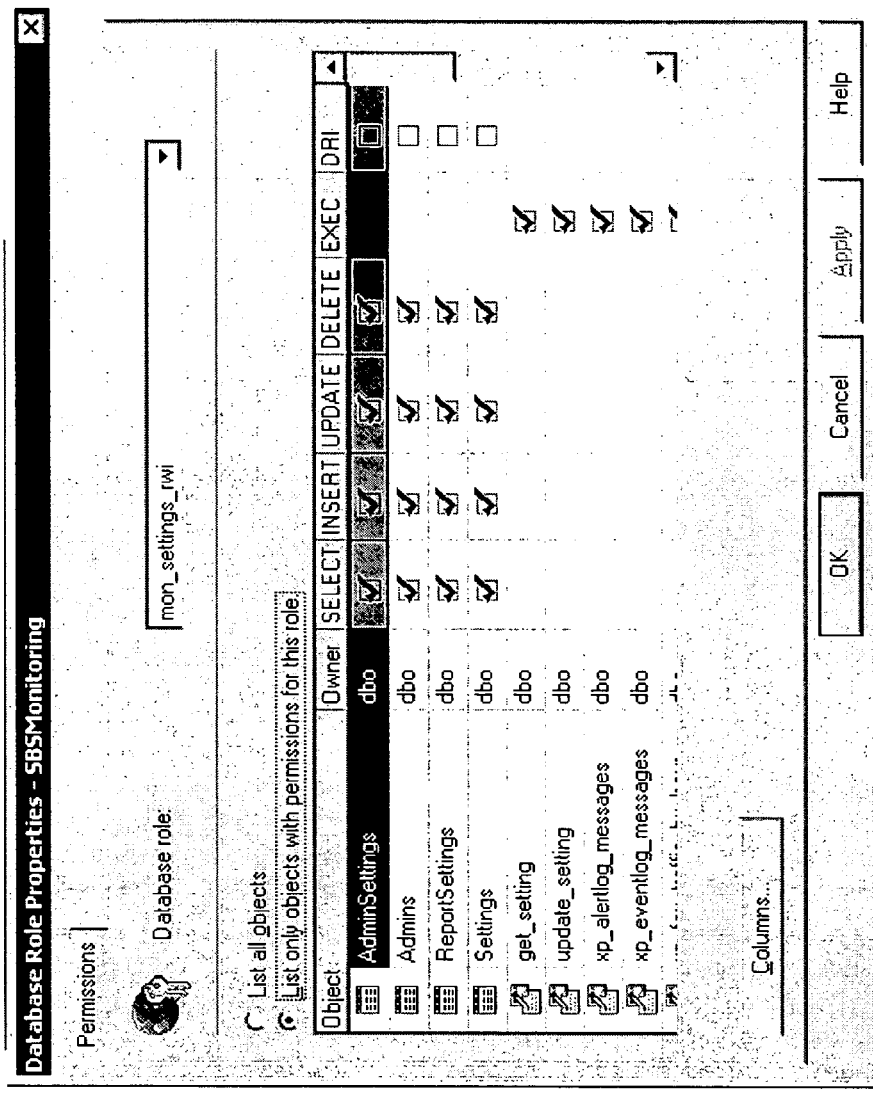
FIG. 30 is a screen shot of a database role property settings user interface in accordance with an aspect of the present invention.

Another instance of the present invention facilitates a user in becoming more proactive in addressing issues with a client's networks through proper monitoring and reporting. It can also configure monitoring and reporting such that a client can have direct report access. A monitoring configuration UI 1700 as illustrated in FIG. 17 can provide a quick and easy way for users to immediately start receiving default monitoring and reports. The UI 1700 improves visibility and usage numbers related to monitoring and allows for easy re-configuration. A mode selection UI is shown in FIG. 18. This is an example of a configuration entry interface that provides further capability to select and/or deselect features such as an option to receive performance reports via e-mail (see reporting options UI 1900 in FIG. 19, for example), an option to view usage reports in a management console (see reporting options UI 1900 in FIG. 19, for example), an option to receive usage reports via e-mail (see reporting options UI 1900 in FIG. 19, for example), an ability to modify e-mail addresses that reports are sent to (see e-mail options UI 2000 in FIG. 20, for example), an ability to modify a list of users that can access a client's website in order to view usage reports from the Intranet (see business owner usage report UI 2100 in FIG. 21, for example), an option to receive health monitor related alerts (see alerts UI 2200 in FIG. 22, for example), an ability to modify e-mail addresses that health monitor related alerts are sent to (see alerts UI 2200 in FIG. 22, for example), and an ability to reconfigure monitoring features from scratch (refer back to mode selection UI 1800 in FIG. 18) and the like. Various properties related to a system, including database properties and roles, can be manipulated as well by a user as illustrated in UI's 2300-3000 shown in FIGS. 23-30. These are meant to be representative examples only and are not meant to limit the scope of the present invention.

Figure 38:
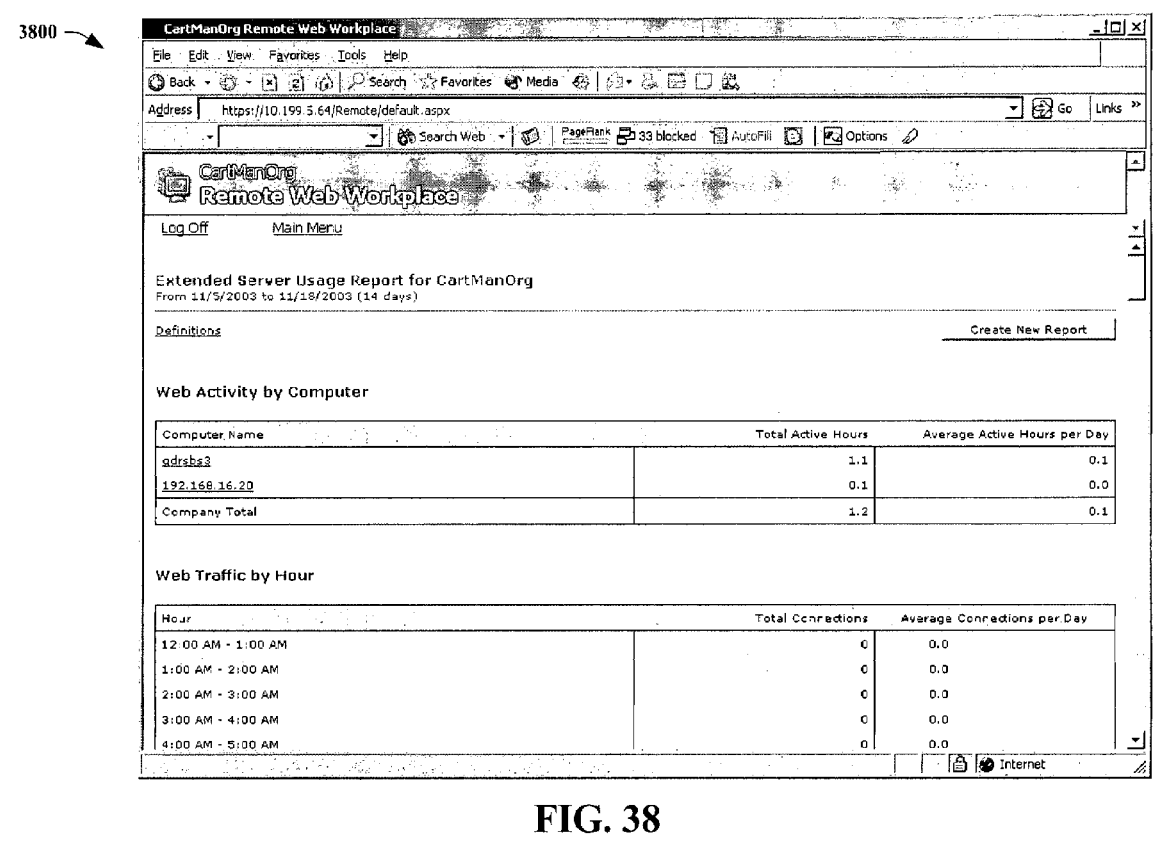
Figure 39:
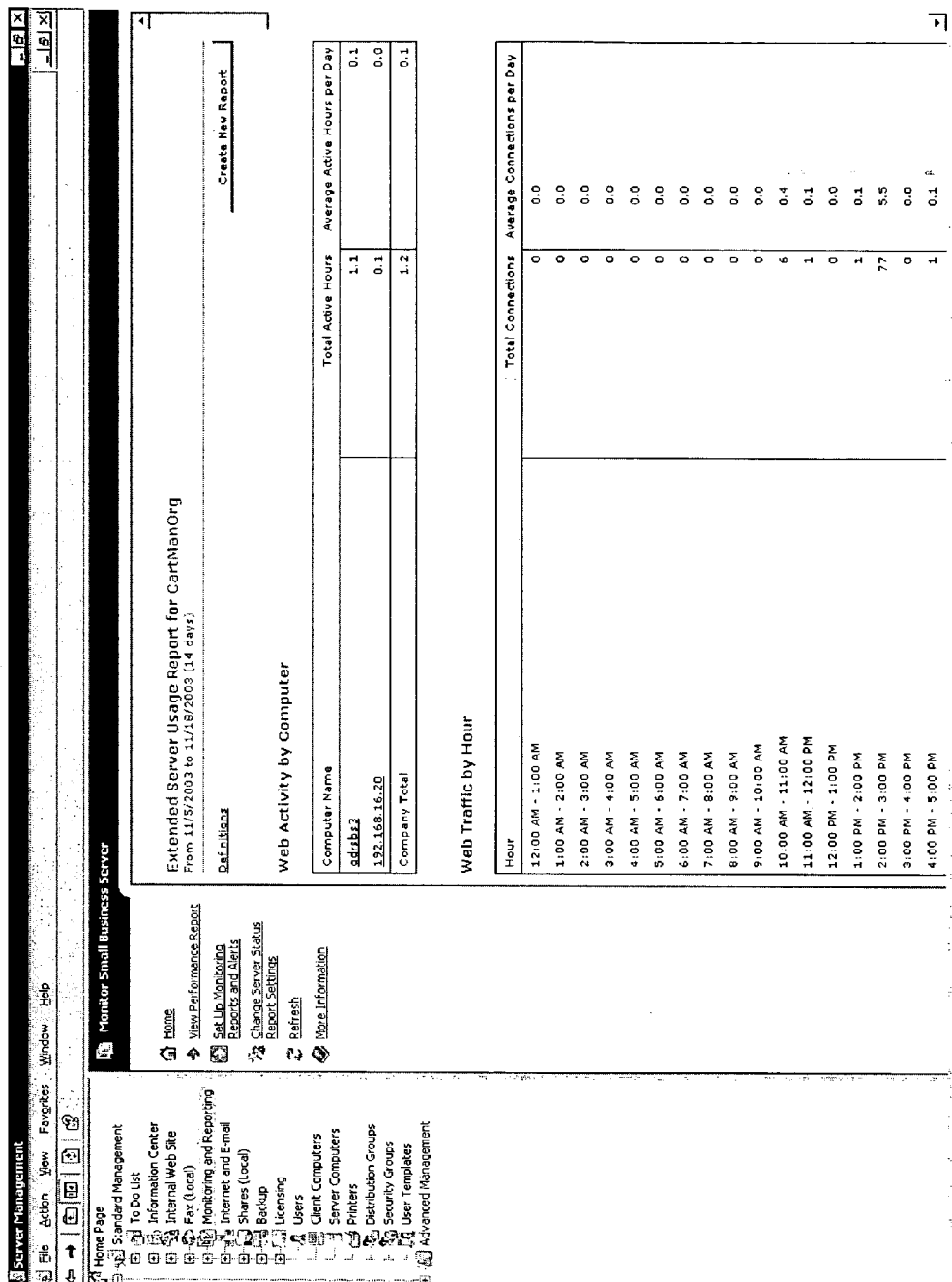
FIG. 39 is a screen shot of a management console user interface in accordance with an aspect of the present invention.

Yet another instance of the present invention facilitates monitoring utilization of a system and/or server and the like. Additional UI's are employed to provide clients with valuable information about utilization of their network by network users, to ensure information is relevant and applicable to clients through re-settable data collection and/or specific data collection time period selections, to provide statistics for a network's core services, to facilitate a new channel of value for users such as VAPs, for example, to account for server and/or network downtime, and to conserve disk space on a network and/or server and the like. A client, with access privileges, can interface with an activity report UI 3100 as shown in FIG. 31. Reports generated by the present invention include, but are not limited to, an e-mail utilization report (see e-mail utilization report UI 3200 in FIG. 32, for example), a fax utilization report (see fax utilization report UI 3300 in FIG. 33, for example), a document utilization report (see document utilization report UI 3400 in FIG. 34, for example), a web utilization report (see web utilization report UI 3500 in FIG. 35, for example), a web access utilization report (see web access utilization report UI 3600 in FIG. 36, for example), and a remote connection utilization report (see remote connection utilization report UI 3700 in FIG. 37, for example) and the like. Although like reports are illustrated together, the present invention can generate reports with more and/or less information and/or mixed types of information. One skilled in the art will appreciate that information generated by the present invention can be presented to a user and/or client by other means and/or in other formats within the scope of the present invention. Reports can also be accessed via a remote user portal UI 3800 as shown in FIG. 38, for example, and/or via a management console UI 3900 illustrated in FIG. 39, for example.

Still yet another instance of the present invention facilitates statusing of servers and/or networks health and/or performance such as reporting performance parameters and errors and the like. An overall summary for a particular server in a network can be provided via an overall server summary performance report UI 4000 such as that shown in FIG. 40. System performance parameters can include, but are not limited to, memory in use, free disk space, busy disk time, and CPU utilization and the like as illustrated in a performance summary report UI 4100 in FIG. 41. Performance parameters can also be grouped into a "Top X" processes in Y amount of time format by individual performance parameters as depicted in a Top 5 performance parameter report UI 4200 shown in FIG. 42. Errors can include, but are not limited to, health monitor alerts (see critical alerts report UI 4400 in FIG. 44), auto services that aren't running (see service failure report UI 4300 in FIG. 43), and event log errors (see critical errors in application log report UI 4400 in FIG. 44) and the like. One skilled in the art will appreciate that information generated by the present invention can be presented to a user and/or client by other means and/or in other formats within the scope of the present invention. Reports can also be accessed via a remote user portal UI 3800 as shown in FIG. 38, for example and/or via a management console UI 3900 illustrated in FIG. 39, for example. Although like reports are illustrated together, the present invention can generate reports with more and/or less information and/or mixed types of information.

Figure 45:
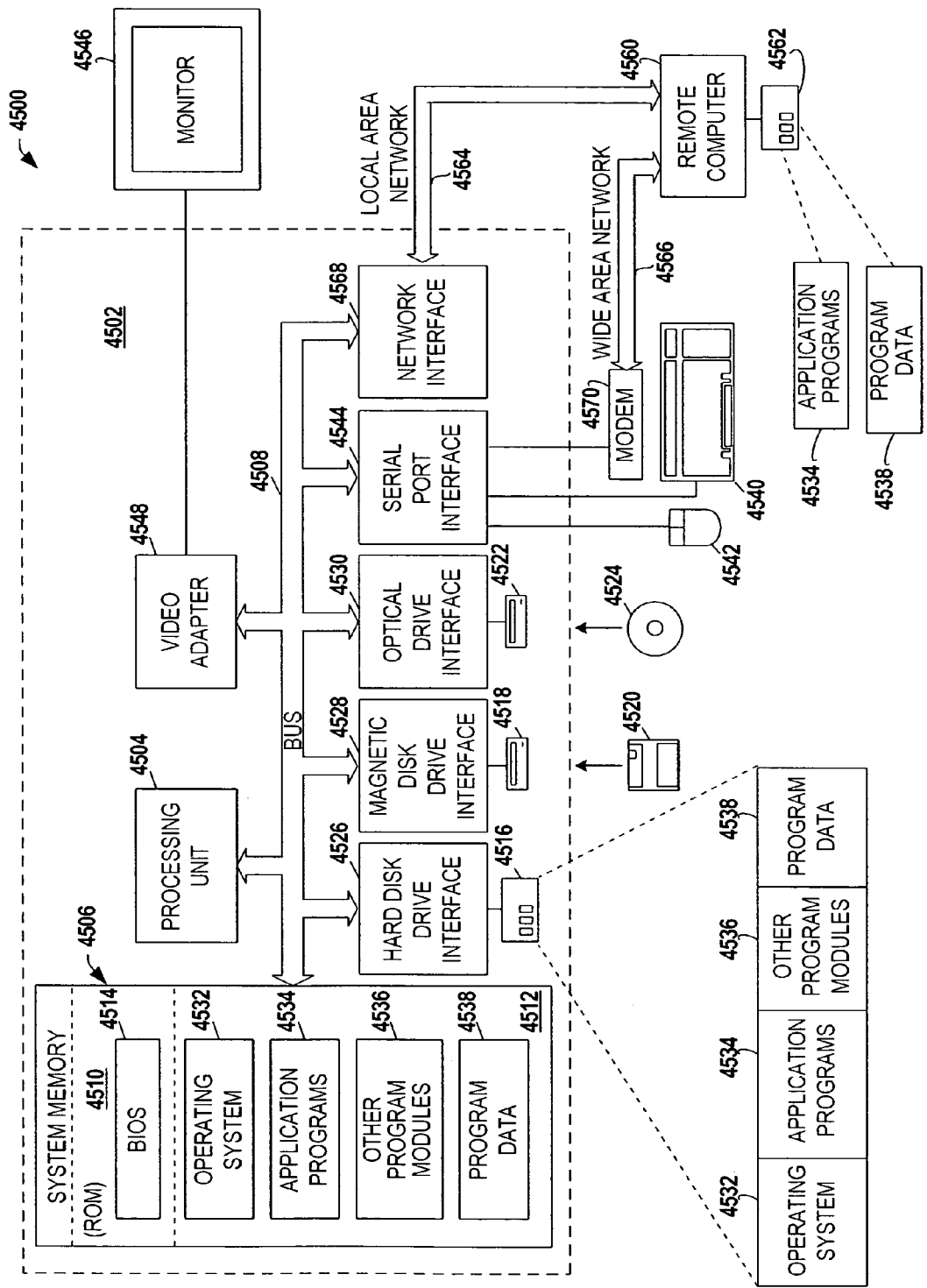
FIG. 45 illustrates an example operating environment in which the present invention can function.

In order to provide additional context for implementing various aspects of the present invention, FIG. 45 and the following discussion is intended to provide a brief, general description of a suitable computing environment 4500 in which the various aspects of the present invention may be implemented. While the invention has been described above in the general context of computer-executable instructions of a computer program that runs on a local computer and/or remote computer, those skilled in the art will recognize that the invention also may be implemented in combination with other program modules. Generally, program modules include routines, programs, components, data structures, etc., that perform particular tasks and/or implement particular abstract data types. Moreover, those skilled in the art will appreciate that the inventive methods may be practiced with other computer system configurations, including single-processor or multi-processor computer systems, minicomputers, mainframe computers, as well as personal computers, hand-held computing devices, microprocessor-based and/or programmable consumer electronics, and the like, each of which may operatively communicate with one or more associated devices. The illustrated aspects of the invention may also be practiced in distributed computing environments where certain tasks are performed by remote processing devices that are linked through a communications network. However, some, if not all, aspects of the invention may be practiced on standalone computers. In a distributed computing environment, program modules may be located in local and/or remote memory storage devices.

As used in this application, the term "component" is intended to refer to a computer-related entity, either hardware, a combination of hardware and software, software, or software in execution. For example, a component may be, but is not limited to, a process running on a processor, a processor, an object, an executable, a thread of execution, a program, and a computer. By way of illustration, an application running on a server and/or the server can be a component. In addition, a component may include one or more subcomponents.

With reference to FIG. 45, an exemplary system environment 4500 for implementing the various aspects of the invention includes a conventional computer 4502, including a processing unit 4504, a system memory 4506, and a system bus 4508 that couples various system components, including the system memory, to the processing unit 4504. The processing unit 4504 may be any commercially available or proprietary processor. In addition, the processing unit may be implemented as multi-processor formed of more than one processor, such as may be connected in parallel.

The system bus 4508 may be any of several types of bus structure including a memory bus or memory controller, a peripheral bus, and a local bus using any of a variety of conventional bus architectures such as PCI, VESA, Microchannel, ISA, and EISA, to name a few. The system memory 4506 includes read only memory (ROM) 4510 and random access memory (RAM) 4512. A basic input/output system (BIOS) 4514, containing the basic routines that help to transfer information between elements within the computer 4502, such as during start-up, is stored in ROM 4510.

The computer 4502 also may include, for example, a hard disk drive 4516, a magnetic disk drive 4518, e.g., to read from or write to a removable disk 4520, and an optical disk drive 4522, e.g., for reading from or writing to a CD-ROM disk 4524 or other optical media. The hard disk drive 4516, magnetic disk drive 4518, and optical disk drive 4522 are connected to the system bus 4508 by a hard disk drive interface 4526, a magnetic disk drive interface 4528, and an optical drive interface 4530, respectively. The drives 4516-4522 and their associated computer-readable media provide nonvolatile storage of data, data structures, computer-executable instructions, etc. for the computer 4502. Although the description of computer-readable media above refers to a hard disk, a removable magnetic disk and a CD, it should be appreciated by those skilled in the art that other types of media which are readable by a computer, such as magnetic cassettes, flash memory cards, digital video disks, Bernoulli cartridges, and the like, can also be used in the exemplary operating environment 4500, and further that any such media may contain computer-executable instructions for performing the methods of the present invention.

A number of program modules may be stored in the drives 4516-4522 and RAM 4512, including an operating system 4532, one or more application programs 4534, other program modules 4536, and program data 4538. The operating system 4532 may be any suitable operating system or combination of operating systems. By way of example, the application programs 4534 and program modules 4536 can include an aggregated system data scheme in accordance with an aspect of the present invention.

A user can enter commands and information into the computer 4502 through one or more user input devices, such as a keyboard 4540 and a pointing device (e.g., a mouse 4542). Other input devices (not shown) may include a microphone, a joystick, a game pad, a satellite dish, wireless remote, a scanner, or the like. These and other input devices are often connected to the processing unit 4504 through a serial port interface 4544 that is coupled to the system bus 4508, but may be connected by other interfaces, such as a parallel port, a game port or a universal serial bus (USB). A monitor 4546 or other type of display device is also connected to the system bus 4508 via an interface, such as a video adapter 4548. In addition to the monitor 4546, the computer 4502 may include other peripheral output devices (not shown), such as speakers, printers, etc.

It is to be appreciated that the computer 4502 can operate in a networked environment using logical connections to one or more remote computers 4560. The remote computer 4560 may be a workstation, a server computer, a router, a peer device or other common network node, and typically includes many or all of the elements described relative to the computer 4502, although, for purposes of brevity, only a memory storage device 4562 is illustrated in FIG. 45. The logical connections depicted in FIG. 45 can include a local area network (LAN) 4564 and a wide area network (WAN) 4566. Such networking environments are commonplace in offices, enterprise-wide computer networks, intranets and the Internet.

When used in a LAN networking environment, for example, the computer 4502 is connected to the local network 4564 through a network interface or adapter 4568. When used in a WAN networking environment, the computer 4502 typically includes a modem (e.g., telephone, DSL, cable, etc.) 4570, or is connected to a communications server on the LAN, or has other means for establishing communications over the WAN 4566, such as the Internet. The modem 4570, which can be internal or external relative to the computer 4502, is connected to the system bus 4508 via the serial port interface 4544. In a networked environment, program modules (including application programs 4534) and/or program data 4538 can be stored in the remote memory storage device 4562. It will be appreciated that the network connections shown are exemplary, and other means (e.g., wired or wireless) of establishing a communications link between the computers 4502 and 4560 can be used when carrying out an aspect of the present invention.

In accordance with the practices of persons skilled in the art of computer programming, the present invention has been described with reference to acts and symbolic representations of operations that are performed by a computer, such as the computer 4502 or remote computer 4560, unless otherwise indicated. Such acts and operations are sometimes referred to as being computer-executed. It will be appreciated that the acts and symbolically represented operations include the manipulation by the processing unit 4504 of electrical signals representing data bits which causes a resulting transformation or reduction of the electrical signal representation, and the maintenance of data bits at memory locations in the memory system (including the system memory 4506, hard drive 4516, floppy disks 4520, CD-ROM 4524, and remote memory 4562) to thereby reconfigure or otherwise alter the computer system's operation, as well as other processing of signals. The memory locations where such data bits are maintained are physical locations that have particular electrical, magnetic, or optical properties corresponding to the data bits.

Figure 46:
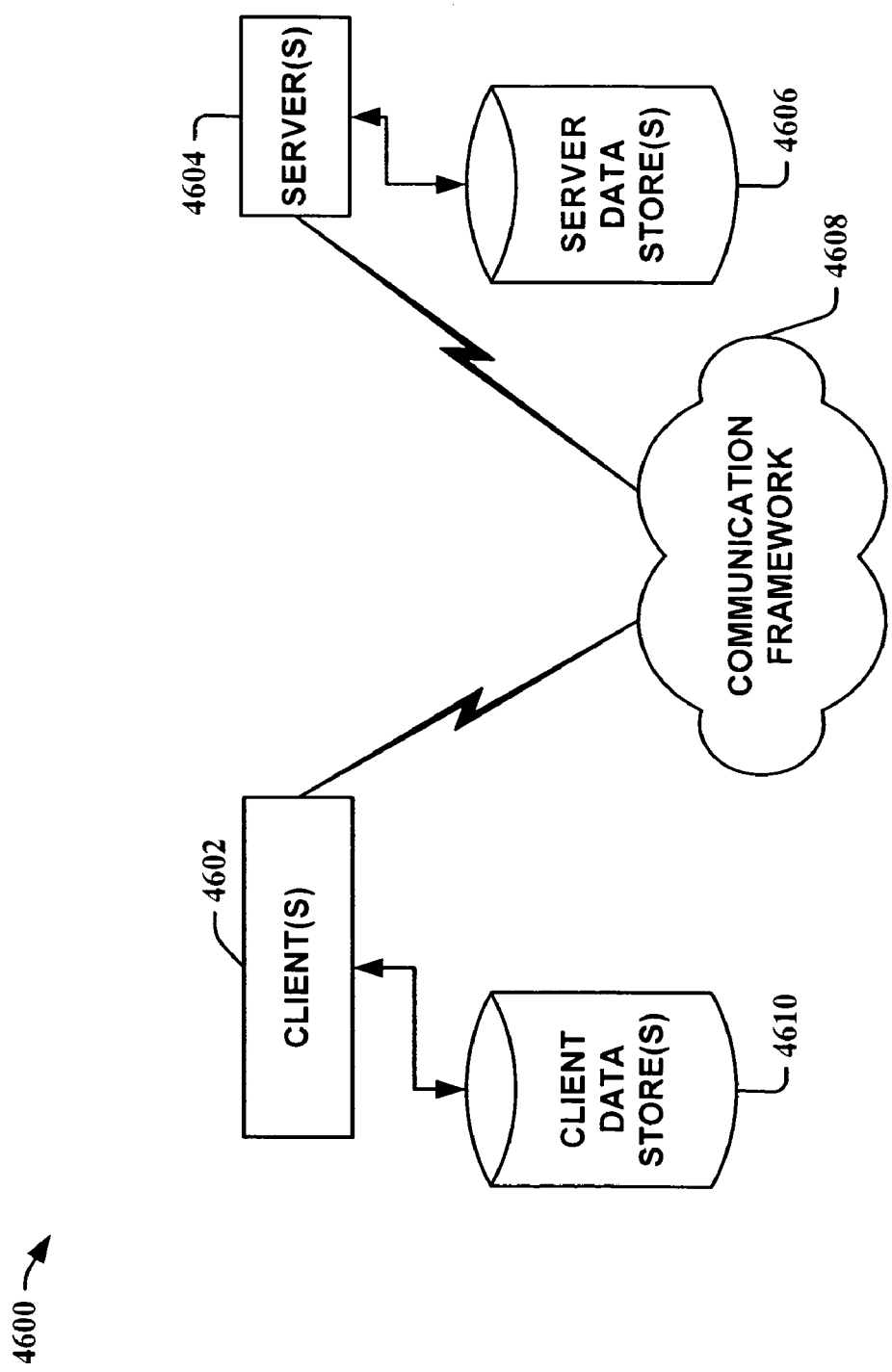
FIG. 46 illustrates another example operating environment in which the present invention can function.

FIG. 46 is another block diagram of a sample computing environment 4600 with which the present invention can interact. The system 4600 further illustrates a system that includes one or more client(s) 4602. The client(s) 4602 can be hardware and/or software (e.g., threads, processes, computing devices). The system 4600 also includes one or more server(s) 4604. The server(s) 4604 can also be hardware and/or software (e.g., threads, processes, computing devices). The servers 4604 can house threads to perform transformations by employing the present invention, for example. One possible communication between a client 4602 and a server 4604 may be in the form of a data packet adapted to be transmitted between two or more computer processes. The system 4600 includes a communication framework 4608 that can be employed to facilitate communications between the client(s) 4602 and the server(s) 4604. The client(s) 4602 are operably connected to one or more client data store(s) 4610 that can be employed to store information local to the client(s) 4602. Similarly, the server(s) 4604 are operably connected to one or more server data store(s) 4606 that can be employed to store information local to the servers 4604.

In one instance of the present invention, a data packet transmitted between two or more computer components that facilitates networked system health alert determination, the data packet is comprised of, at least in part, information relating to health alert monitoring of a networked system, the information including, at least in part, aggregated health related data that is time-averaged data of health related parameters corresponding to at least one system component of the networked system.

In another instance of the present invention, a data packet transmitted between two or more computer components that facilitates networked system state determination, the data packet is comprised of, at least in part, information relating to a state of a networked system, the state determined via aggregation and analysis of data from at least a subset of system components of the networked system.

In yet another instance of the present invention, a data packet transmitted between two or more computer components that facilitates networked system monitoring, the data packet is comprised of, at least in part, information relating to monitoring of a networked system, the information including, at least in part, state related data based, at least in part, upon aggregated state data corresponding to at least one system component of the networked system.

It is to be appreciated that the systems and/or methods of the present invention can be utilized in aggregating system data for facilitating computer components and non-computer related components alike. Further, those skilled in the art will recognize that the systems and/or methods of the present invention are employable in a vast array of electronic related technologies, including, but not limited to, computers, servers and/or handheld electronic devices, and the like.

What has been described above includes examples of the present invention. It is, of course, not possible to describe every conceivable combination of components or methodologies for purposes of describing the present invention, but one of ordinary skill in the art may recognize that many further combinations and permutations of the present invention are possible. Accordingly, the present invention is intended to embrace all such alterations, modifications and variations that fall within the spirit and scope of the appended claims. Furthermore, to the extent that the term "includes" is used in either the detailed description or the claims, such term is intended to be inclusive in a manner similar to the term "comprising" as "comprising" is interpreted when employed as a transitional word in a claim.

What is claimed is:

1. A method that facilitates monitoring health of a networked system, comprising:
    obtaining system information from at least one computing device on the networked system based at least in part on aggregation rules, the system information includes at least one of at least one of system health data, system usage data or system performance data, the system information obtained from at least one of a health monitor alert, a registry, a running process or logs;

aggregating the obtained information to provide at least one average value for one or more desired data parameters included in the obtained system information;

storing the aggregated information in a data store;

providing automatic control of the at least one computing device based at least in part on the aggregated system information and control parameters that specify control responses, the control responses include at least one of default control responses or programmed control responses selected based upon the aggregated system information;

presenting reports in accordance with report parameters, the reports include the aggregated information, at least one of the presented reports comprising recommendations for setting health monitor alert value; and notifying at least one user of a condition identified in the aggregated information, the notification is based at least in part on contact rules that specify conditions that require notifications and identities of the at least one user.

2. A system that facilitates health monitoring of a networked system, comprising:

at least one processor coupled to memory that executes:

a data gather component that obtains system information from at least one computing device, the data gather component aggregates the obtained system information based at least in part on aggregation parameters, the system information includes at least one of system health data, system usage data or system performance data;

a control component that provides automatic control of the at least one computing device based at least in part on the aggregated system information, the automatic control includes at least one of default control responses or programmed control responses, the control component utilizes control parameters that specify control responses based upon the aggregated information; and a user interface that presents reports that include the aggregated information in accordance with report parameters, the user interface further enables modification of the aggregation parameters, the control parameters or the report parameters, at least one of the presented reports comprising recommendations for setting health monitor alert value.

3. The system of claim 2, the system component comprises a server.

4. The system of claim 2, at least one of the presented reports comprising, at least in part, at least one alert based on utilization of an average value of a desired data parameter of the aggregated system information and a substantially instantaneous value of the desired data parameter.

5. The system of claim 2, at least one of the presented reports comprising, at least in part, health monitoring alerts.

6. The system of claim 2, at least one of the presented reports comprising, at least in part, administrative guidance information corresponding to the networked system.

7. The system of claim 6, the administrative guidance information comprising, at least in part, recommendations for setting health monitor alert thresholds.

8. The system of claim 2, at least one of the presented reports comprises a rolling time-averaged value of a desired data parameter and a current health monitor alert threshold setting related to the desired data parameter.

9. The system of claim 8, the rolling time-average value comprising a time Averaged value over a 30 day period.

10. The system of claim 2, the aggregated information includes a rolling time-averaged value of a data parameter of the system information.

11. The system of claim 10, the rolling time-averaged value comprising a time averaged value over a 30 day time period.

12. The system of claim 2, the user interface comprising a customizable user interface.

13. The system of claim 2, the user interface comprising an interactive user interface.

14. The system of claim 13, the interactive user interface comprising a user interface that provides an input for setting a health monitor alert threshold value.

15. The system of claim 13, the interactive user interface comprising a user interface that provides manual control of health monitor alerts in addition to automatic control.

16. The system of claim 15, the control of the health monitor alerts comprising control of at least one selected from the group consisting of when health monitor alerts are displayed and what health monitor alerts are displayed.

17. The system of claim 15, the control of the health monitor alerts comprising control of health monitor alert notification.

18. The system of claim 17, the control of the health monitor alert notification comprising control of who is notified when a health monitor alert occurs.

19. The system of claim 18, the control of who is notified comprising at least one selected from the group comprising a system administrator of the networked system and an owner of the networked system.

20. The system of claim 17, the control of the health monitor alert notification comprising control of how notification occurs.

21. The system of claim 20, the control of how notification occurs comprising control of at least one selected from the group consisting of an email, a paging device, and a direct user interface display.

22. A system employing at least one system of claim 2 that provides a unified information source of health monitoring data for a plurality of networked systems.

23. A computer readable storage medium having stored thereon computer executable components of the system of claim 2.

24. A device employing the system of claim 2 comprising at least one selected from the group consisting of a computer, a server, and a handheld electronic device.

25. A system that facilitates health monitoring of a networked system, comprising:

means for obtaining and aggregating system information from at least one computing device on the networked system based at least in part on aggregation rules, the system information includes at least one of at least one of system health data, system usage data or system performance data;

means for providing automatic control of the at least one computing device based at least in part on the aggregated system information and control parameters that specify control responses, the control responses include at least one of default control responses or programmed control responses selected based upon the aggregated system information;

means for presenting reports in accordance with report parameters, the reports include the aggregated information, at least one of the presented reports comprising recommendations for setting health monitor alert value; and means for modifying the aggregation parameters, the control parameters or the report parameters.

* * * * *